(12) United States Patent
Thompson et al.

(10) Patent No.: US 8,435,268 B2
(45) Date of Patent: May 7, 2013

(54) SYSTEMS, DEVICES AND METHODS FOR THE CORRECTION OF SPINAL DEFORMITIES

(75) Inventors: Matthew Thompson, Corte Madera, CA (US); Hiram Chee, Santa Cruz, CA (US); Richard Ginn, Gilroy, CA (US); David White, Morgan Hill, CA (US)

(73) Assignee: Reduction Technologies, Inc., Corte Madera, CA (US)

( * ) Notice: Subject to any disclaimer, the term of this patent is extended or adjusted under 35 U.S.C. 154(b) by 835 days.

(21) Appl. No.: 12/178,530

(22) Filed: Jul. 23, 2008

(65) Prior Publication Data

US 2009/0105766 A1    Apr. 23, 2009

Related U.S. Application Data

(63) Continuation-in-part of application No. 11/656,314, filed on Jan. 19, 2007.

(51) Int. Cl.
*A61B 17/88*    (2006.01)

(52) U.S. Cl.
USPC .......................................... 606/279; 606/248

(58) Field of Classification Search .................... 606/60, 606/246, 248, 254–263, 277–279
See application file for complete search history.

(56) References Cited

U.S. PATENT DOCUMENTS

| | | |
|---|---|---|
| 2,774,350 A | 12/1956 | Cleveland, Jr. |
| 4,697,582 A | 10/1987 | William |
| 4,773,402 A | 9/1988 | Asher et al. |
| 5,201,734 A | 4/1993 | Cozad et al. |
| 5,290,289 A | 3/1994 | Sanders et al. |
| 5,391,168 A | 2/1995 | Sanders et al. |
| 5,413,576 A | 5/1995 | Rivard |
| 5,540,689 A | 7/1996 | Sanders et al. |
| 5,586,983 A | 12/1996 | Sanders et al. |
| 5,591,165 A | 1/1997 | Jackson |
| 5,630,816 A | 5/1997 | Kambin |
| 5,672,175 A | 9/1997 | Martin |
| 5,733,284 A | 3/1998 | Martin |
| 5,938,662 A | 8/1999 | Rinner |
| 5,951,553 A | 9/1999 | Betz et al. |
| 6,015,409 A | 1/2000 | Jackson |
| 6,136,000 A | 10/2000 | Louis et al. |
| 6,287,308 B1 | 9/2001 | Betz et al. |
| 6,299,613 B1 | 10/2001 | Ogilvie et al. |
| 6,554,831 B1 | 4/2003 | Rivard et al. |
| 6,616,669 B2 | 9/2003 | Ogilvie et al. |

(Continued)

FOREIGN PATENT DOCUMENTS

| | | |
|---|---|---|
| WO | WO 2004/017705 A2 | 3/2004 |
| WO | WO 2005/013839 A2 | 2/2005 |

OTHER PUBLICATIONS

WO, Written Opinion, PCT/US08/000416, Jul. 2, 2008.
WO, Written Opinion, PCT/US09/050594, Oct. 28, 2009.

(Continued)

*Primary Examiner* — Ellen C Hammond
(74) *Attorney, Agent, or Firm* — Dickstein Shapiro LLP

(57) ABSTRACT

Provided herein are systems, devices and methods for the correction of spinal deformities with the use one or more implantable rods configured to apply a corrective force to the spine. Methods of minimally invasive implantation of a corrective system are provided, such as where the corrective system is attached only to the spinous process of one or more vertebral bodies. Various corrective systems as well as components thereof are also provided.

16 Claims, 32 Drawing Sheets

U.S. PATENT DOCUMENTS

| | | | |
|---|---|---|---|
| 6,623,484 | B2 | 9/2003 | Betz et al. |
| 6,783,527 | B2 | 8/2004 | Drewry et al. |
| 6,802,844 | B2 | 10/2004 | Ferree |
| 6,986,771 | B2 | 1/2006 | Paul et al. |
| 6,989,011 | B2 | 1/2006 | Paul et al. |
| 7,125,410 | B2 | 10/2006 | Freudliger |
| 2004/0143264 | A1 | 7/2004 | McAfee |
| 2004/0215192 | A1 | 10/2004 | Justis et al. |
| 2005/0143823 | A1 | 6/2005 | Boyd et al. |
| 2005/0182409 | A1 | 8/2005 | Callahan et al. |
| 2005/0203519 | A1 | 9/2005 | Harms et al. |
| 2006/0015181 | A1 | 1/2006 | Elberg |
| 2006/0036244 | A1 | 2/2006 | Spitler et al. |
| 2006/0122620 | A1 | 6/2006 | Kim |
| 2006/0195087 | A1 | 8/2006 | Sacher et al. |
| 2006/0229607 | A1 | 10/2006 | Brumfield |
| 2006/0229612 | A1 | 10/2006 | Rothman et al. |
| 2006/0253121 | A1 | 11/2006 | Gorensek et al. |
| 2006/0282077 | A1 | 12/2006 | Labrom et al. |
| 2007/0016188 | A1 | 1/2007 | Boehm, Jr. et al. |
| 2007/0043355 | A1 | 2/2007 | Bette et al. |
| 2007/0043358 | A1 | 2/2007 | Molz, IV et al. |
| 2007/0055244 | A1 | 3/2007 | Jackson |
| 2007/0078461 | A1 | 4/2007 | Shluzas |
| 2007/0093814 | A1 | 4/2007 | Callahan, II et al. |
| 2007/0118118 | A1 | 5/2007 | Kwak et al. |
| 2007/0162007 | A1 | 7/2007 | Shoham |
| 2007/0270809 | A1 | 11/2007 | Drewry et al. |
| 2008/0021466 | A1 | 1/2008 | Shadduck et al. |
| 2008/0091201 | A1 | 4/2008 | Reiley |
| 2008/0108990 | A1 | 5/2008 | Mitchell et al. |
| 2008/0177326 | A1 | 7/2008 | Thompson |
| 2008/0183209 | A1 | 7/2008 | Robinson et al. |
| 2008/0195153 | A1 | 8/2008 | Thompson |

OTHER PUBLICATIONS

WO, Written Opinion, PCT/US10/037785, Aug. 3, 2010.

US, Office Action, U.S. Appl. NO. 11/656,314, Sep. 29, 2010.

Butterwick et al., Lidocaine Levels During the First Two Hours of Infiltration of Dilute Anesthetic Solution for Tumescent Liposuction: Rapid Versus Slow Delivery, Dermatol. Surg. 29:9, pp. 681-685, Sep. 1999.

Cohn et al., Ambulatory Phlebectomy Using the Tumescent Technique for Local Anesthesia, Dermatol. Surg. 1995:21, pp. 315-318, 1995.

Kim et al., The Influence of Fixation Rigidity on Intervertebral Joints—An Experimental Comparison Between a Rigid and a Flexible System, J. Korean Neurosurg. Soc. 37:364-369, May 2005.

Seiger, Ambulatory Phlebectomy: Tumescent Anesthesia Concerning Method of Infiltration, Letters to the Editor, Dermatol. Surg. 24:936 (1998).

Wever et al., The Surgical Correction of Scoliosis with Shape-Memory Metal, Shape Memory Implants, Ecole Polytechnique de Montreal, Ph.D.L. Yahia, pp. 129-146, 2000.

WO, PCT/US2009/05094—Search Report and Written Opinion, Oct. 28, 2009.

Akbarnia et al., Dual Growing Rod Technique for the Treatment of Progressive Early-Onset Scoliosis, Spine vol. 30, No. 175, pp. S46-S57, 2005.

Aubin et al., Biomechanical Modeling of Posterior Instrumentation of the Scoliotic Spine, Computer Methods in Biomechanics and Biomedical Enginnering, vol. 6(1), pp. 27-33, 2003.

Baumgart et al., Zur Dwyerschen Skoliosenoperation mittels Drähten aus Memory-Legierungen, Arch. Orth. Traum. Surg. 91, pp. 67-75, Feb. 10, 1978 (abstract provided).

Betz et al., An Innovative Technique of Vertebral Body Stapling for the Treatment of Patients With Adolescent Idiopathic Scoliosis: A Feasability, Safety, and Utility Study, Spine vol. 28, No. 205, pp. S255-S265, 2003.

Betz et al., Preclinical Testing of a Wedge-Rod System for Fusionless Correction of Scoliosis, Spine vol. 28, No. 205, pp. S275-S278, 2003.

Blakemore et al., Submuscular Isola Rod With or Without Limited Apical Fusion in the Management of Severe Spinal Deformities in Young Children, Spine vol. 26, No. 18, pp. 2044-2048, 2001.

Braun et al., Creation of an Experimental Idiopathic-Type Scoliosis in an Immature Goat Model Using a Flexible Posterior Asymmetric Tether, Spine vol. 31, No. 13, pp. 1410-1414, 2006.

Braun et al., Experimental Scoliosis in an Immature Goat Model: A Method That Creates Idiopathic-Type Deformity With Minimal Violation of the Spinal Elements Along the Curve, Spine vol. 28, No. 19, pp. 2198-2203, 2003.

Braun et al., Fusionless Scoliosis Correction Using a Shape Memory Alloy Staple in the Anteiror Thoracic Spine of the Immature Goat, Spine vol. 29, No. 18 pp. 1980-1989, 2004.

Braun, et al., Mechanical Modulation of Vertebral Growth in the Fusionless Treatment of Progressive Scoliosis in an Experimental Model, Spine vol. 31, No. 12, pp. 1314-1320, 2006.

Braun, et al., Relative Versus Absolute Modulation of Growth in the Fusionless Treatment of Experimental Scoliosis, Spine vol. 31, No. 16, pp. 1776-1782, 2006.

Braun, et al., The Efficacy and Integrity of Shape Memory Alloy Staples and Bone Anchors with Ligament Tethers in the Fusionless Treatment of Experimental Scoliosis, The Journal of Bone & Joint Surgery, vol. 87-A, No. 9, Sep. 2005.

Braun et al., Three-Dimensional Analysis of 2 Fusionless Scoliosis Treatments: A Flexible Ligament Tether *Versus* a Rigid-Shape Memory Alloy Staple, Spine vol. 31, No. 3, pp. 262-268, 2006.

Janicki et al., A Comparison of the Thoracolumbosacral Orthoses and Providence Orthosis in the Treatment of Adolescent Idiopathic Scoliosis, Pediatr. Orthop., vol. 27, No. 3, Jun. 2007.

Lu et al., Treatment of Scoliosis with a Shape-Memory Alloy Rod, Zhonghua Wai Ke Za Zhi, vol. 24, No. 3, pp. 129-131, 187, Mar. 1986 (abstract provided).

Matsumoto et al., Correction of Scoliosis with Shape-memory Alloy, J. Jpn. Orthop. Assoc., vol. 67, No. 4, pp. 267-274, 1993.

Puttlitz et al., A Biomechanical Assessment of Thoracic Spine Stapling, Spine vol. 32, No. 7, pp. 766-771, 2007.

Rohlmann et al., Flexible non-fusion scoliosis correction systems reduce intervertebral rotation less than rigid implants and allow growth of the spine: a finite element analysis of different features of orthobiom™, Eur. Spine J. (2008) 17:217-223.

Sanders et al., A Preliminary Investigation of Shape Memory Alloys in the Surgical Correction of Scoliosis, Spine vol. 18, No. 11, pp. 1640-1644, 1993.

Schmerling et al., Using the Shape Recovery of Nitinol in the Harrington Rod Treatment of Scoliosis, J. Biomed. Mater. Res., vol. 10, pp. 879-892, 1976.

Wever et al., Scoliosis correction with shape-memory metal: results of an experimental study, Eur. Spine J. (2002) 11:100-106.

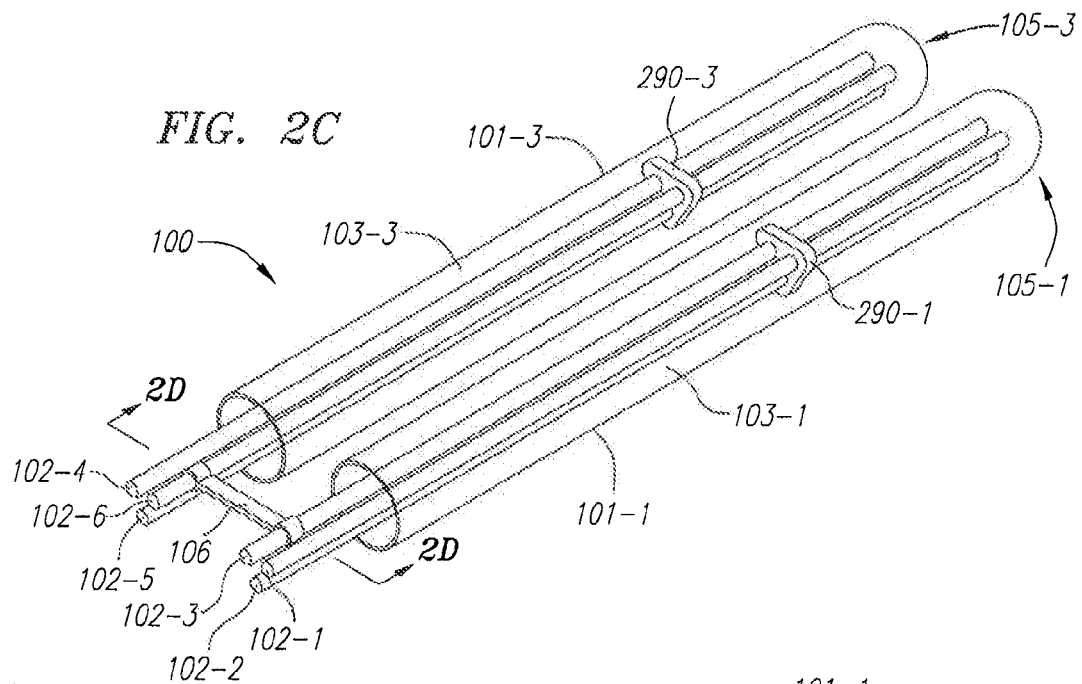
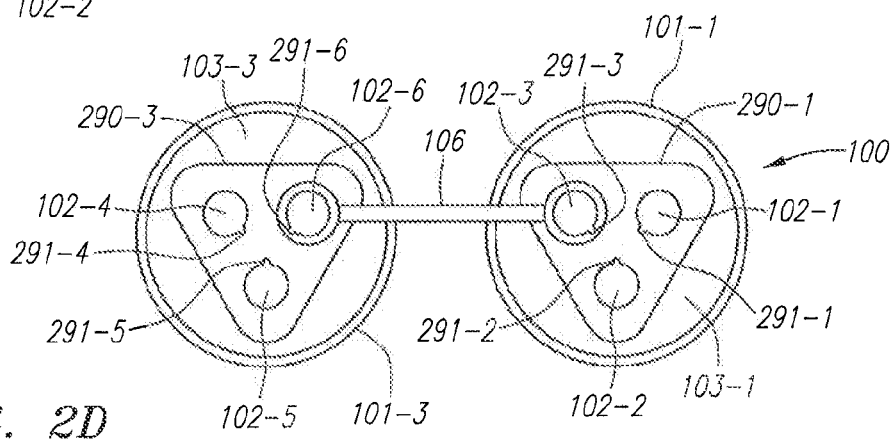
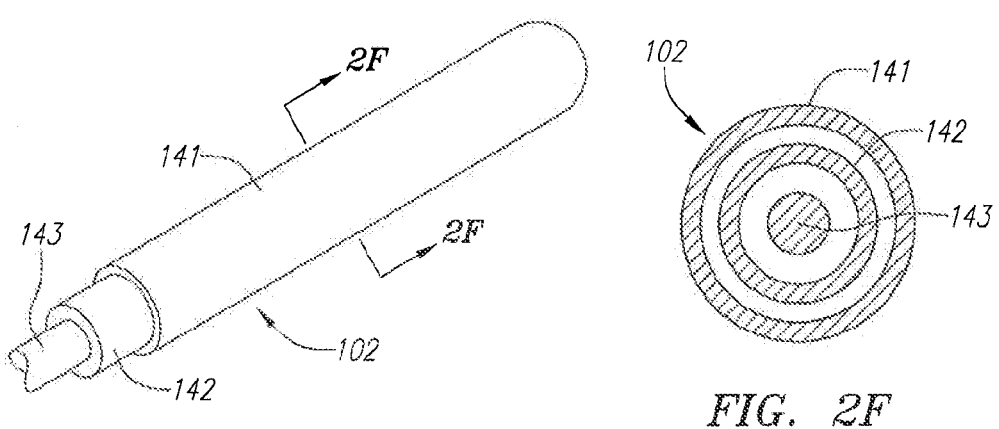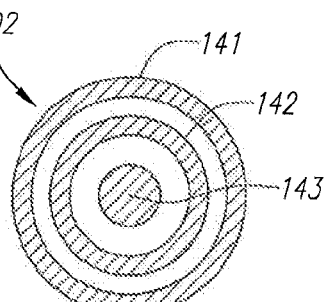
FIG. 2C
FIG. 2D
FIG. 2E
FIG. 2F

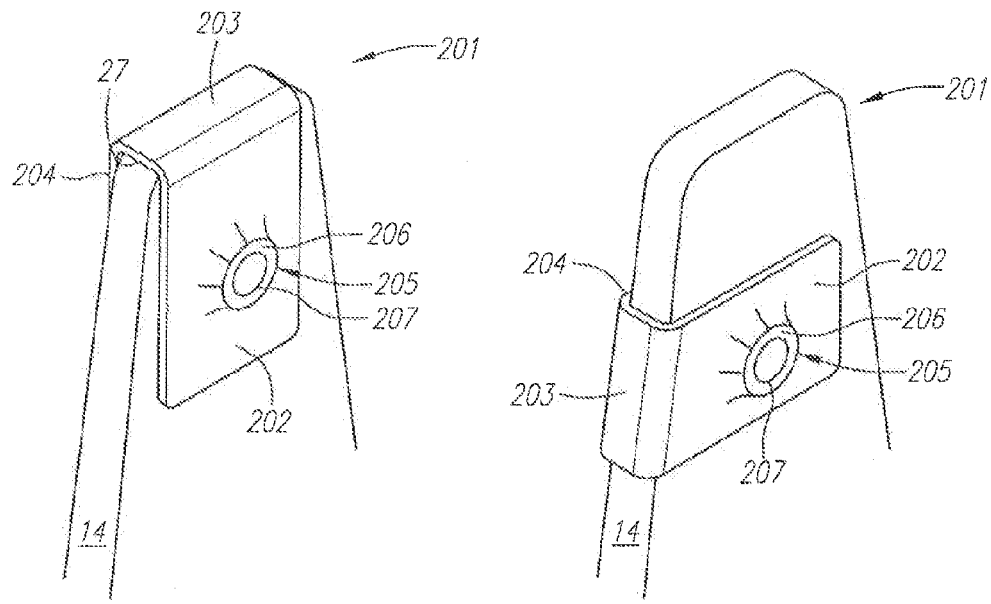
*FIG. 4A*  *FIG. 4B*
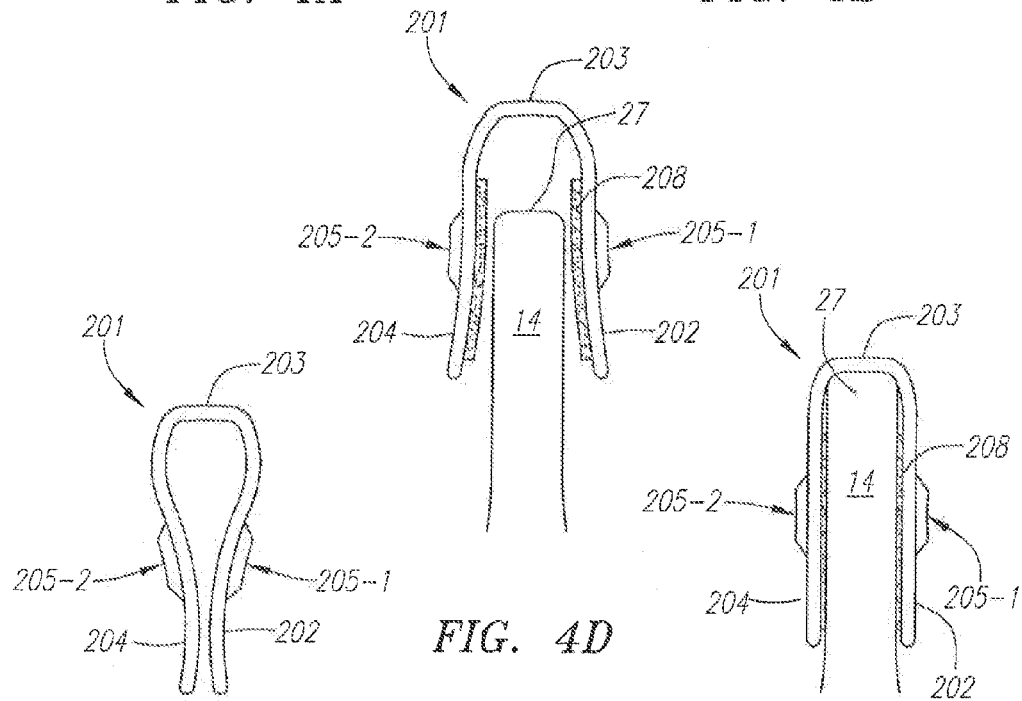
*FIG. 4C*  *FIG. 4D*  *FIG. 4E*

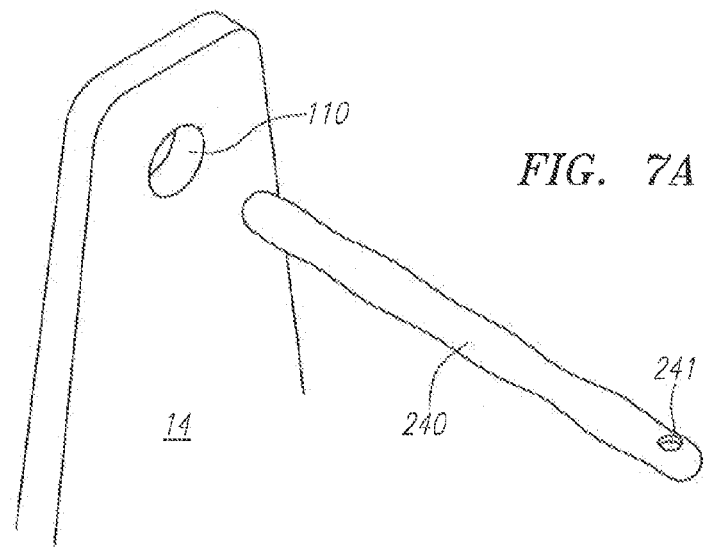
FIG. 7A
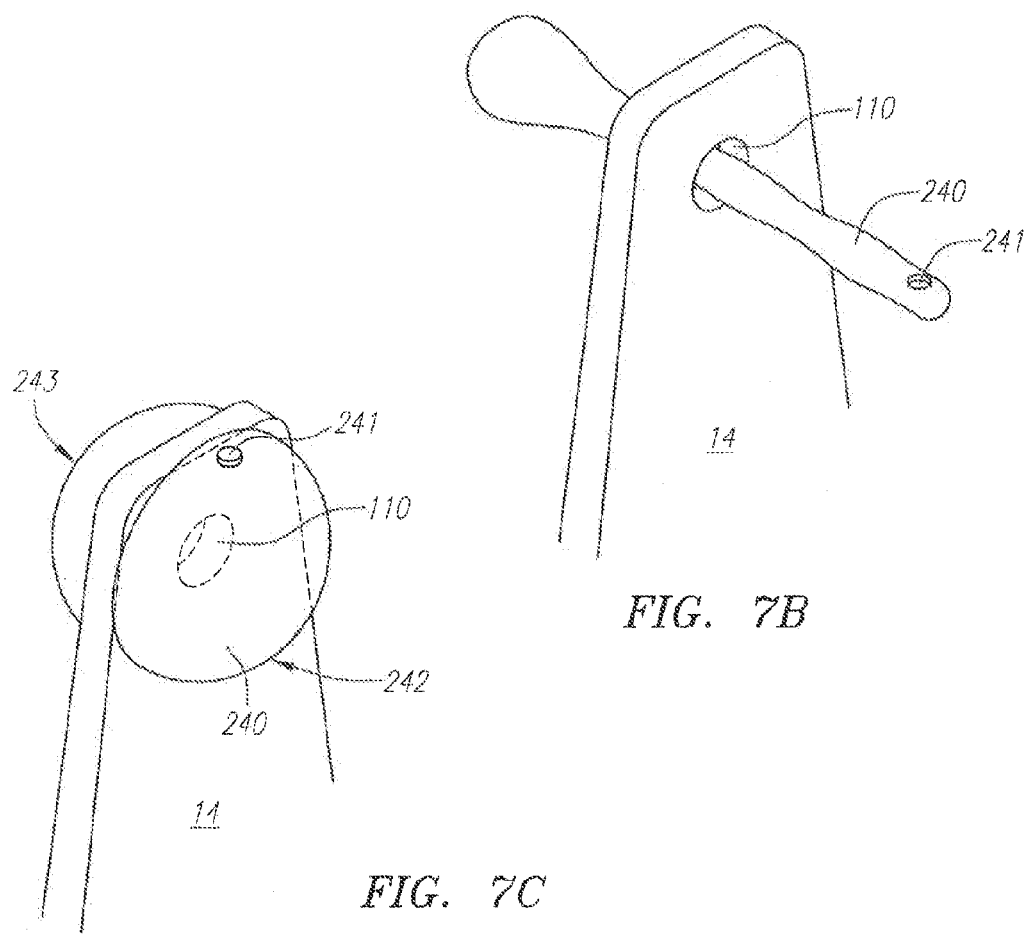
FIG. 7B
FIG. 7C

SYSTEMS, DEVICES AND METHODS FOR THE CORRECTION OF SPINAL DEFORMITIES

CROSS-REFERENCE TO RELATED APPLICATIONS

This application is a continuation-in-part of U.S. patent application Ser. No. 11/656,314, filed Jan. 19, 2007 and entitled "Orthosis to Correct Spinal Deformities," which is incorporated by reference herein in its entirety.

FIELD OF THE INVENTION

The subject matter described herein relates generally to the correction of spinal deformities.

BACKGROUND OF THE INVENTION

Scoliosis is a disease which deforms the spine affecting more girls than boys and manifesting itself during the teen years when significant growth is experienced. Scoliosis generally combines a horizontal torsion and flexion in a frontal plane and develops in three spatial dimensions. As noted, the disease generally begins with the growth phase as it is hypothesized that this is probably due to the rotation of one or two vertebral bodies.

Sufferers of scoliosis are generally treated initially with a rigid corset-like orthopedic brace. If this treatment proves unsuccessful, another treatment option can include spinal fusion through invasive surgery. Spinal fusion can oftentimes largely correct a spinal deformity, but can also result in complications, such as when the patient advances into adult life.

Yet another option is the implantation of a treatment apparatus intended to treat the deformity without spinal fusion. Like spinal fusion, this implantation can require significantly invasive surgery, including the dissection of the paraspinous muscles off of the vertebral body and exposure of the facet joints and laminae. Typical treatment devices include one and oftentimes two rods mounted on either side of the spinal column. If two rods are employed, anchoring means are provided for positioning the rods in spaced-apart parallel alignment. Hooks or screws are employed to anchor the rods along the selected portion of the spinal column for treatment, typically requiring relatively deep penetration of the cortical bone above one or both of the pedicles. The anchors are rigidly locked to the associated rod to prevent relative motion there between and the entire arrangement can be supplemented with bone grafts. Such an invasive procedure can lead to increased blood loss, generation of scar tissue and induces the risk that the vertebral bodies will auto-fuse.

Others have suggested improvements to the orthosis described above. For example, U.S. Pat. No. 6,554,831 suggests a system that allows for intra-operative correction and micro-movement of the vertebrae despite implantation of a corrective rod. The '831 patent suggests use of a rigid rod that does not allow a patient to flex or extend post-operatively until the corrective rod is removed requiring additional surgery. Anchoring to the transverse process is also taught thus requiring significant invasive surgery and consequent fusion.

U.S. Pat. No. 5,672,175 suggests another approach which theoretically provides a patient with close to normal range of motion of the vertebrae by instrumenting the spine with elastic members pre-curved to correct the spinal deformity. Anchoring to the transverse process is also employed which, again, is a major drawback in performing the techniques suggested in the '175 patent. Further, this device theoretically overcomes the deformity with constant force applied by pre-curved correction members but this does not allow for resultant changes in the deformity or tissue relaxation. Because of the use of these pre-curved rods, the technique suggested in the '175 patent may actually result in a final deformity completely opposite to the original deformity due to tissue growth and relaxation. Furthermore, this device risks alteration of the natural biomechanics of the spine by fixing the distance between points of attachment. This prohibits any change in distance between pedicles, which shifts the center of rotation of each affected vertebral body anteriorly.

U.S. Pat. No. 4,697,582 suggests a correction apparatus which employs an elastic rod or a pair of elastic rods exhibiting a memory shape of the corresponding part of a normal rachis, the rods being immobilized in rotation in each of its guidance openings. However, the mechanical assembly suggested in the '582 patent is appended to an area on each vertebrae between the spinal process and transverse process, which, again, results in significant invasive surgery, (as discussed earlier) and can result in fusion of vertebral bodies in the to-be corrected region.

Therefore, a spinal correction system is needed to correct spinal deformities while eliminating or significantly reducing the drawbacks of conventional systems.

SUMMARY

Provided herein are systems, devices and methods for the correction of spinal deformities with the use one or more implantable rods configured to apply a corrective force to the spine. These systems, devices and methods are provided herein by way of exemplary embodiments, which are in no way intended to limit the subject matter beyond that of the express language of the appended claims.

Numerous minimally invasive implantation methods are provided, including attachment of the spinal correction system to the patient's spinal column without exposure of the vertebral facet joints. In other embodiments, attachment occurs only to the spinous process of one or more vertebral bodies with varying degrees of invasiveness. Also, exemplary embodiments of corrective systems and devices and methods for attachment of the system are provided.

Other systems, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the exemplary embodiments be construed as limiting the appended claims, absent express recitation of those features in the claims.

BRIEF DESCRIPTION OF THE FIGURES

The details of the subject matter set forth herein, both as to its structure and operation, may be gleaned in part by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIGS. 2C-D are cross-sectional views depicting exemplary embodiments of a spinal correction system.

FIG. 2E is a perspective view depicting an exemplary embodiment of a spinal correction system.

FIG. 2F is a cross-sectional view taken along line 2F-2F of FIG. 2E.

FIG. 3C is a side view depicting an exemplary embodiment of a spinal correction system implanted within a patient.

FIGS. 4A-B are perspective views depicting exemplary embodiments of attachment devices.

FIGS. 4C-E are perspective views depicting exemplary embodiments of attachment devices during implantation.

FIGS. 7A-C are perspective views depicting stages of implantation of an exemplary embodiment of an attachment device.

DETAILED DESCRIPTION

Figures 1A, 1B:
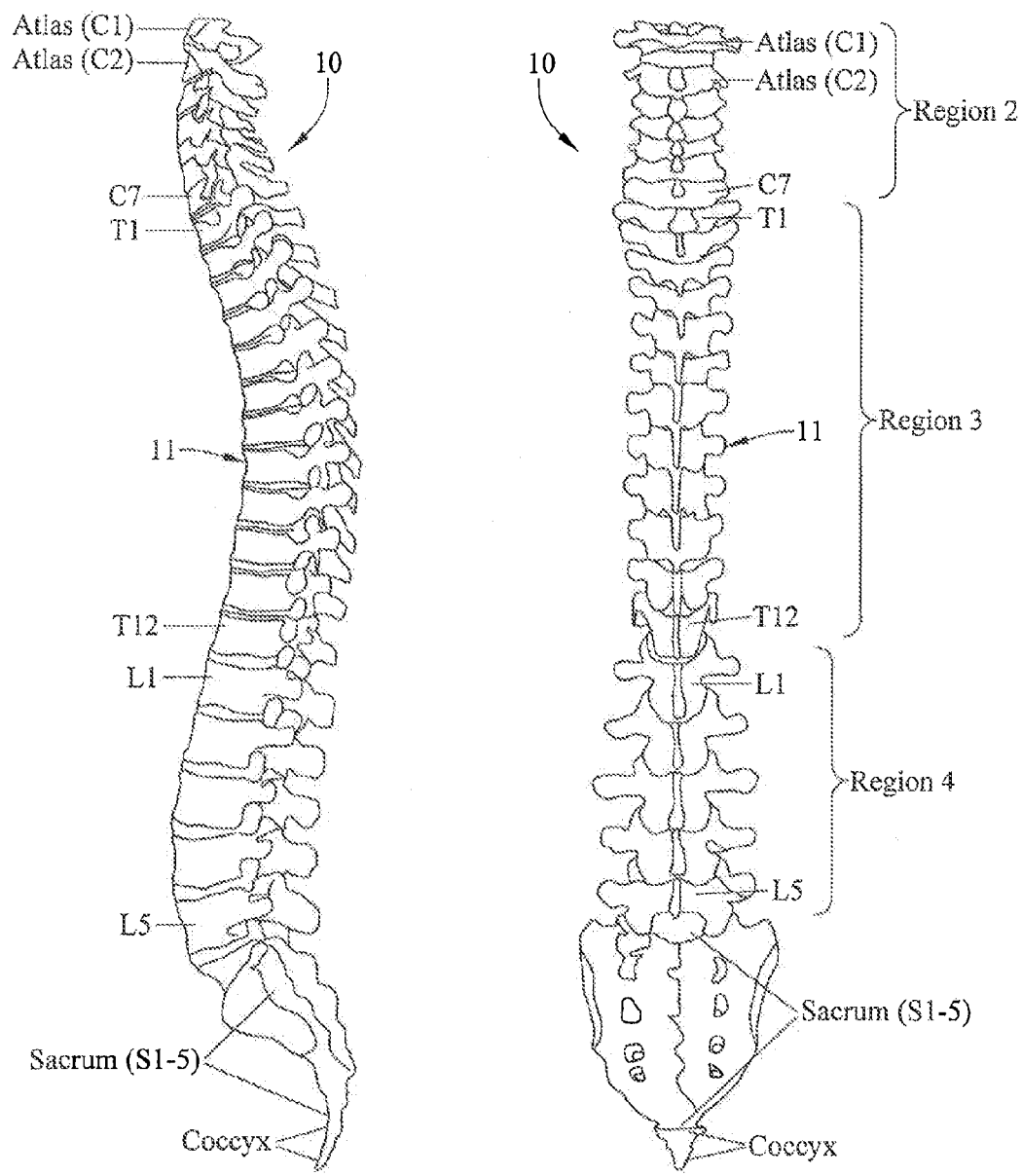
FIG. 1A is a lateral view of an exemplary spinal column.
FIG. 1B is a posterior view of an exemplary spinal column.

To facilitate the description of the systems, devices and methods provided herein, a discussion will first be set forth of basic healthy spinal anatomy and deformities that can occur thereto. FIG. 1A is a lateral view of a normal human spinal column 10. Spinal column 10 is divided into three principal regions. The top, or superior, region 2 includes seven vertebral bodies 11 and is referred to as the "cervical" region of the spine. These seven bodies are consecutively labeled C1-C7. The intermediate region 3 includes twelve vertebral bodies 11 and is referred to as the "thoracic" region of the spine. These twelve bodies are consecutively labeled T1-T12. The bottom, or inferior, region 4 includes five vertebral bodies 11 and is referred to as the "lumbar" region. These five bodies are consecutively labeled L1-L5.

In a general sense, a typical healthy spinal column 10 has curvature in the sagittal plane (depicted in FIG. 1A) but not in the coronal plane (depicted in the posterior view of FIG. 1B). Referring to FIG. 1A, from a posterior perspective, the curvature of cervical region 2 and lumbar region 4 can be generally described as concave (lordotic), while the curvature of thoracic region 3 can be generally described as convex (kyphotic). Spinal deformities occur when the curvature in any of regions 2-4 changes to an undesirable degree, inhibiting the patient's appearance and/or ability to move and possibly causing pain and/or disfunction of the nervous system, as well as other symptoms.

Spinal deformities can result from excessive curvature, insufficient curvature or straightening ("flat-back") or even reversal of the curvature of any or all of the spinal regions 2-4 in the sagittal plane, as well as the introduction of lateral (i.e., side-to-side) curvature of any or all of the regions 2-4 in the coronal plane. For instance, excessive kyphotic curvature of thoracic region 3 of the spine is referred to as hyper-kyphosis and excessive lordotic curvature of lumbar region 4 is referred to as hyper-lordosis. Lateral curvature in any of regions 2-4 is generally referred to as scoliosis. Particularly severe spinal deformities, such as scoliosis, can also include pronounced rotation of the vertebral bodies 11. These deformities can involve complex variations from the alignment of a healthy spine in all three spatial dimensions and can occur across the entire length of the spine.

Figure 1C:
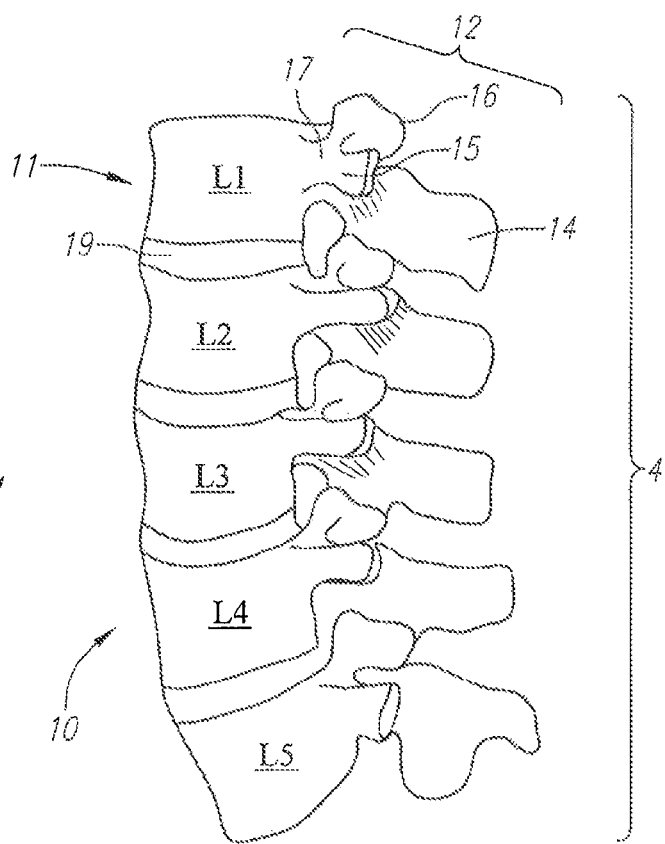
FIGS. 1C-D are lateral views of an exemplary portions of a spinal column.

FIG. 1C is a lateral view of lumbar region 4 of a spinal column 10 showing the five lumbar vertebral bodies 11 (labeled L1-L5, respectively), each separated by an intervertebral disc 19. Each vertebral body 11 includes a posterior portion 12 having numerous bony features. The most prominent feature is spinous process 14, which is an elongate, somewhat quadrilateral, fin-shaped feature that is situated the farthest posteriorly from each vertebral body 11. Located adjacent to spinous process 14 are left and right transverse processes 15 and left and right mamillary processes 16 (only the left side of each is shown here). These processes 14-16 are connected to each vertebral body 11 by way of left and right pedicles 17 (again, only left side shown).

Figure 1E:
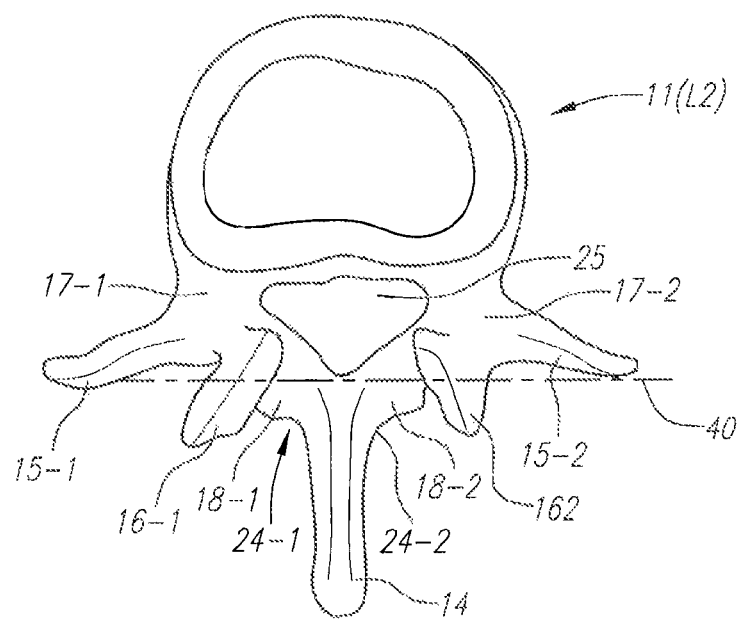
FIG. 1E is superior view of an exemplary vertebral body.
Figure 1D:
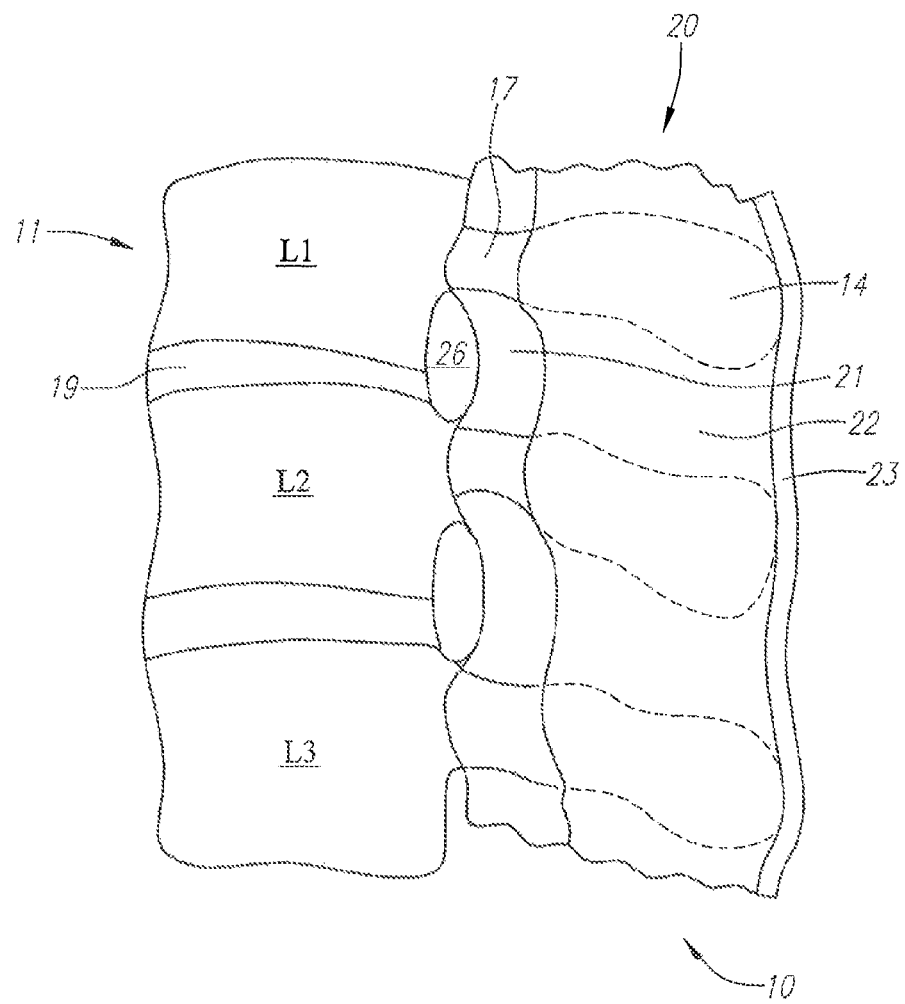

FIG. 1D is a lateral view of three lumbar vertebrae L1-L3 of spinal column 10 with the left side pedicles 17 and processes 15-16 omitted to allow depiction of the interspinous tissue 20. Located adjacent each vertebral body 11 and generally anterior to spinous process 14 (indicated as being obscured by dashed lines) is ligamentum flavum 21, which is immediately adjacent the intervertebral foramen 26. Posterior to ligamentum flavum 21, is the wider interspinous ligament 22 which extends along each side of each spinous process 14. Posterior to interspinous ligament 22 is supraspinous ligament 23, which generally extends along the posterior edge of each spinous process 14 and the interspinous tissue 20.

FIG. 1E is a top down view of a lumbar vertebral body 11. Here, left and right pedicles 17-1 and 17-2 can be seen in greater detail extending away from vertebral body 11. With regards to the reference scheme used herein, generally, specific ones of a similar element (e.g., left and right pedicles 17-1 and 17-2) will be referred to using the appendix -#, where the # corresponds to a specific one (e.g., 1, 2, 3 . . . N) of a similar element. When general references are made to the elements such that identification of the specific ones is not required, then the -# appendix will be omitted.

Also shown is spinous process 14, left and right transverse processes 15-1 and 15-2, mamillary processes 16-1 and 16-2 and left and right laminae 18-1 and 18-2. The spinous process 14 converges with each lamina 18-1 and 18-2 within a laterally disposed flaring transitional region. This convergence occurs generally along the apex 24-1 and 24-2 of each flaring transitional region, respectively. Anterior to each lamina 18 is a space referred to as the vertebral foramen 25. It is through the vertebral foramen 25 (shown in FIG. 1E) and intervertebral foramen 26 (shown in FIG. 1D) that the spinal cord and other spinal nerves (not shown) are routed.

Figure 1F:
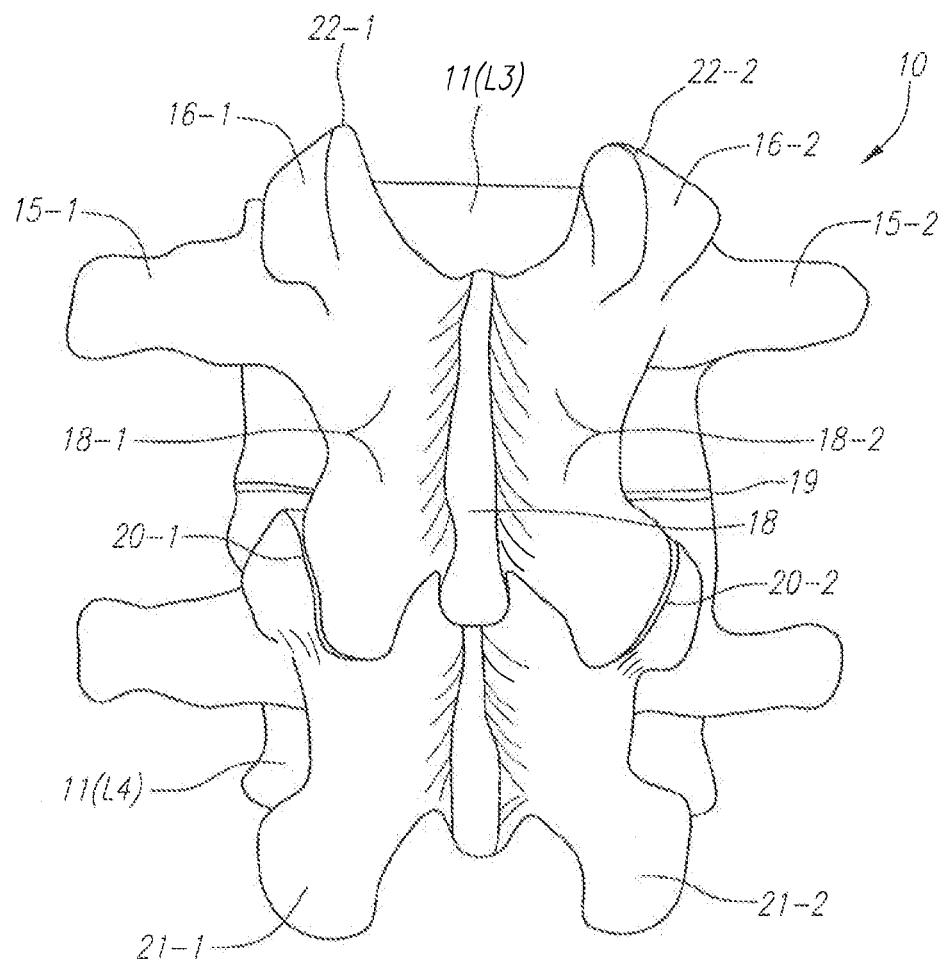
FIG. 1F is a posterior view of an exemplary portion of a spinal column.

FIG. 1F is a posterior view of two vertebral bodies 11, specifically L3 and L4. Left transverse process 15-1 and right transverse process 15-2 are shown extending laterally from each side of bodies 11. Superior to transverse processes 15 are mamillary processes 16-1 and 16-2 and superior articular processes 22-1 and 22-2. Posterior to transverse processes 15 are the left and right laminae 18-1 and 18-2, respectively. At the base of each vertebral body 11 are inferior articular processes 21-1 and 21-2. The joint or interface between superior articular processes 22 and inferior articular processes 21 of the adjacent vertebral body 11 is referred to as facet joint 20, of which a left facet joint 20-1 and a right facet joint 20-2 are depicted here between L3 and L4. Each vertebral body 11 has two sets of facet joints 20, formed in part by the superior articular process 22 at one end and the inferior articular process 21 at the opposite end.

Facet joints 20 are hinge-like and link adjacent vertebral bodies 11 together. Facet joints 20 are referred to as synovial joints, which means that each joint 20 is typically surrounded by a capsule of connective tissue and produces a fluid to nourish and lubricate the joint. The joint surfaces are coated with cartilage to allow smooth motion articulation between adjacent bodies. Dissection of tissue from, and/or exposure of, the facet joint 20 can lead to autofusion, especially in younger patients. Autofusion is the internal fusion of adjacent vertebral bodies 11 together by the patient's own body, and severely deficits the patient's freedom of motion. Autofusion can also be caused by exposure of one or both of the laminae 18.

The systems, devices and methods provided herein are configured to correct spinal deformities through the application of corrective forces to the spinal column. Preferably, one or more flexible, shape memory rods are implanted in close proximity to the spinal column. The rods are preferably formed from metals or metal alloys such as nickel-titanium alloys (e.g., nitinol), titanium, elgiloy, stainless steel, and the like, or polymeric materials such as Liquid Crystal Polymers (LCP), polyetheretherketone (PEEK), tert-butyl acrylate, poly(ethylene glycol) dimethacrylate, polyetherurethane, and the like. The polymeric materials may be modified to increase their strength and toughness with fillers, such as fiber, graphite, and the like. Unless otherwise noted, this description will be of a system incorporating dual rods located on opposite sides of the spinal column.

These rods are preferably preshaped or shape set to a curvature that when applied to a deformity results in a healthy spine. For example, for treatment of each of the three regions of the spinal column, the rods are configured with kyphotic curvature in the portion corresponding to the thoracic region and lordotic curvature in the portions corresponding to the cervical and lumber regions. The rods are then distorted during placement over the deformed portion of the spine such that the rods then apply a corrective force to the spine. Thus, even if the spinal deformity bridges into multiple regions of the spine (cervical, thoracic, lumber), the rods are configured to correct for those corresponding changes in lordosis and kyphosis.

Preferably, correction occurs by the use of only one set of implanted rods over the course of treatment, although correction can also be achieved by way of iterative replacement of the rods. In such an embodiment, the first set of rods can be shaped to correct some, but not all, of the deformity in the spinal column (or can be shaped or sized to resemble a healthy spine but with relatively less strength such that it applies corrective force at a relatively lower level). After that set of rods has been implanted for a length of time sufficient to cause the incremental correction, a new set of rods can be implanted with a shape (or strength) that is configured to achieve incrementally more correction. This process can be repeated as many times as needed until the spinal column is corrected to the desired extent. The use of an iterative process requires multiple surgeries, but can allow for the use of rods that are relatively more flexible, thereby allowing the patient greater freedom in movement. The iterative process also allows the shape of the rods and location of implantation to be fine tuned to exert corrective forces where they are needed to achieve the desired outcome.

Figure 2A:
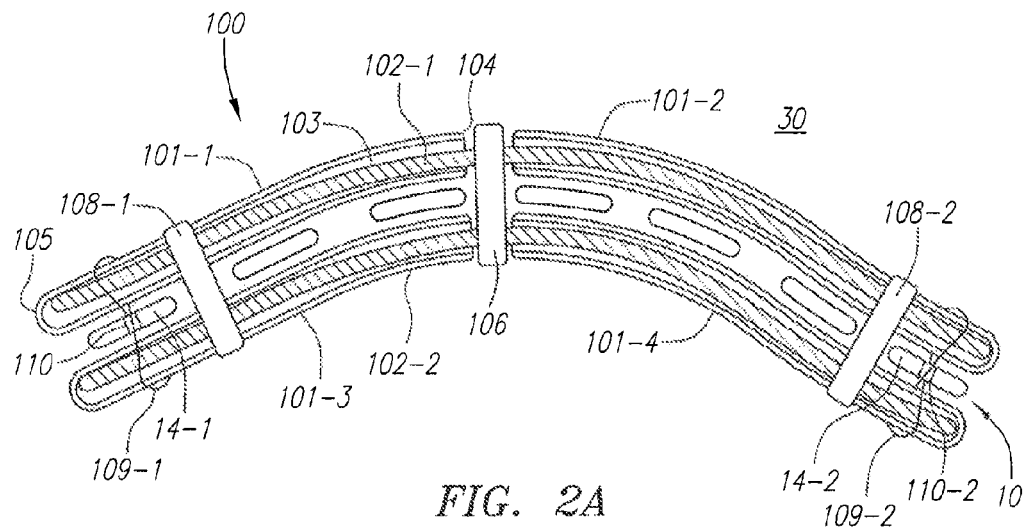
FIG. 2A is a posterior view depicting an exemplary embodiment of a spinal correction system implanted within a patient.

FIG. 2A depicts an exemplary embodiment of a spinal correction system 100 implanted within a body 30 of a patient. Here, system 100 includes tubular members 101, each having an inner lumen 103 for slidably receiving a rod 102. Here, each rod 102 is received within two tubular members 101, although it should be noted that any number of one or more tubular members 101 can be used for each rod 102. For ease of description, tubular members 101 will be referred to herein as sleeves.

There are at least several benefits for using sleeve 101 outside of rod 102. Sleeve 101 facilitates the placement or replacement of rods 102 by forming a readily accessible pathway for rod 102 into the implantation space. The new rod would also not require attachment to the spinous process, as the sleeve 101 is preferably already attached.

Also, avoidance of rigid attachment to the bone can be desired since fixing any member to bone can potentially put large, localized forces on the bone in the areas of contact. As corrective rods 102 can be long, they provide the opportunity to place large moments on the rigid attachment. Allowing rods 102 limited lateral and rotational freedom of movement within sleeves 101 reduces the stress placed on the rigid attachment. Sleeves 101 also isolate bone and tissue from frictional forces generated by the moving rod 102. Sleeves 101 can also contain and isolate any wear particles that may be generated by movement of rods 102.

Figure 2B:
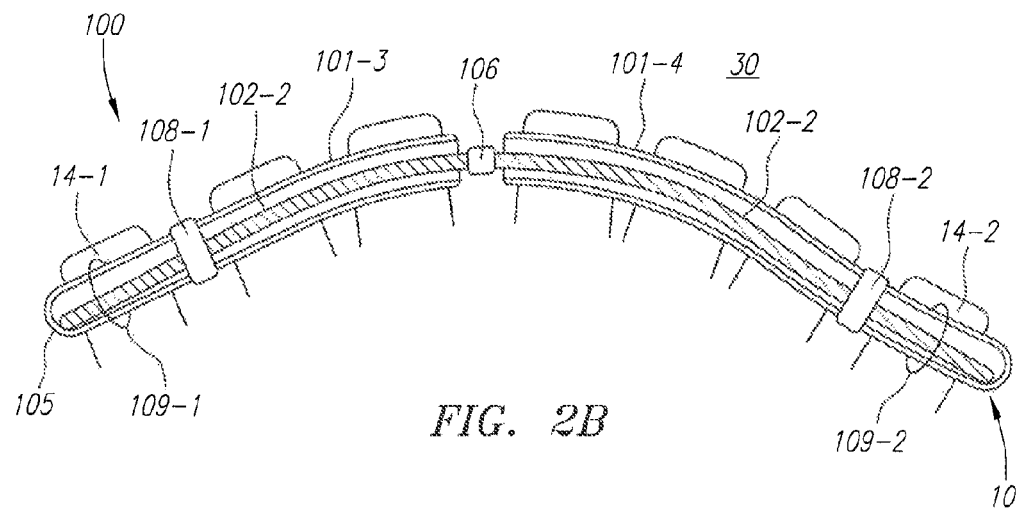
FIG. 2B is a lateral view depicting an exemplary embodiment of a spinal correction system implanted within a patient.

FIG. 2A is a posterior view of system 100 implanted along spinal column 10. FIG. 2B is a lateral view of the embodiment of FIG. 2A showing rod 102 and sleeve 101 on the left side of the spinal column 10. As shown in FIG. 2A, this example of spinal column 10 exhibits a scoliotic bend to the patient's right for which correction is desired (patient's head is to the left as shown). In this embodiment, system 100 includes four sleeves 101-1 through 101-4 and two rods 102-1 and 102-2. Sleeves 101 are shown in cross-section to show rod 102 within. Preferably, each sleeve 101 has an open end 104 for receiving rod 102 and a closed end 105. Lumen 103 is sized to slidably receive rod 102 while at the same time allowing limited rotational or lateral movement of rod 102 within lumen 103. Sleeves 101 are preferably formed from a polymeric material such as polyethylene (PE), polypropylene, polyetheretherketone (PEEK), polytetrafluoroethylene (PTFE), fluorinated ethylene/propylene copolymers (FEP), silicones, hydrogels, hydrophilic coatings, polyurethane (PU), polyethylene ptherethalate (PET), polyimide, styrene-ethylene-butadiene styrene (SEBS), and the like.

Sleeves 101 can also be formed from coiled wire or ribbon or can be configured as slotted tubes (either polymeric or metallic). The pattern of the coil or slotted tube can be optimized for flexibility and pushability. Sleeves 101 can be coated with lubricious coatings, such as, hydrophilic coatings to facilitate advancement of the sleeve through the surrounding anatomy and to facilitate introduction or removal of the rods within the sleeves.

Here, rod 102-1 is received within superiorly located sleeve 101-1 and inferiorly located sleeve 101-2. Likewise, rod 102-2 is received within superiorly located sleeve 101-3 and inferiorly located sleeve 101-4. Sleeves 101 and rods 102 preferably extend a sufficient amount past the most superiorly and inferiorly vertebral bodies 11 to be treated in order to accommodate growth and the full range of motion in any direction (i.e. flexion and extension, rotation and bending). Sleeves 101 are arranged such that a gap exists to expose rods 102 such that a rigid rod connector, or coupling device, 106 can be coupled with each rod 102 to hold rods 102 in position relative to each other and prevent each rod from rotating significantly with respect to each other and with respect to the spinal column. For instance, prevention of rotation with respect to the spinal column precludes the curved portion of the rod from rotating out of the sagittal plane and into the coronal plane to accommodate the deformity.

Although spaces are shown between sleeves 101-1 and 101-3 as well as sleeves 101-2 and 101-4 to allow direct coupling of rod connector 106 with each rod 102, this space can be omitted and sleeves 101-1 and 101-3 can be one continuous sleeve (likewise for sleeves 101-2 and 101-4). Direct connection to rods 102 can be foregone with some other measure to prevent rod rotation applied. Alternatively, apertures can be provided in the sleeves to allow access to rods 102. Preferably, only one rigid rod connector 106 is applied between rods 102-1 and 102-2, at a centrally-located position. However, if desired, any number of rigid rod connectors 106 can be applied at any location along the length of system 100.

Each superiorly located sleeve 101-1 and 101-3 can be optionally coupled together by way of a lateral coupling device 108-1. Similarly, the inferiorly located sleeves 101-2 and 101-4 can be coupled together by way of a lateral coupling device 108-2. Coupling device 108 acts to maintain sleeves 101 in position with respect to each other (e.g., so as to prevent sleeves 101 from migrating laterally and also to allow the force applied from a rod on the convex side to act on the deformity). Coupling device 108 can have any configuration suitable for the needs of the application. Here, coupling device 108 is configured as a band. Any number of coupling devices 108 can be applied at any location along the length of system 100.

In addition, sleeves 101 can be coupled with spinal column 10 by way of a spinal coupling device 109. Here, a superiorly located spinal coupling device 109-1 couples sleeves 101-1 and 101-3 to a spinous process 14-1. Specifically, spinal coupling device 109-1 is routed through an iatrogenic, or man-made, opening 110-1, in spinous process 14-1. Opening 110 can be formed by a piercing element (e.g., guidewire, trocar, and the like) or a drill-like element. An exemplary instrument for piercing the spinous process is described in the copending U.S. Patent Application Ser. No. 60/988,432, filed Feb. 7, 2008 and entitled "Hand-held Instruments That Access the Spinous Process of a Vertebrae," which is fully incorporated by reference herein. Spinal coupling device 109 can be also be configured to be secured partially or entirely around the spinous process rather than through it. Spinal coupling device 109 prevents sleeve 101-1 and 101-3 (and, likewise, superior ends of rods 102-1 and 102-2) from migrating posteriorly away from spinal column 10 during flexion of spinal column 10. In some circumstances, spinal coupling device 109 can also prevent sleeves 101 from migrating anteriorly during spinal extension.

An inferiorly located spinal coupling device 109-2 couples sleeves 101-2 and 101-4 together through iatrogenic opening 110-2 within an inferiorly located spinous process 14-2. Coupling device 109 can have any configuration suitable for the needs of the application. Here, coupling device 109 is configured as a tether. Although only coupling device 109 is shown coupled with the patient's spinal column 10, rod coupling device 106 can be optionally coupled to the patient's spinal column (e.g., spinous process) as well.

Preferably, system 100 is only coupled to the spinal column at one superiorly located position and one inferiorly located position, in order to allow significant freedom of movement to the patient. However, system 100 can be coupled with the spinal column at additional locations (e.g., a central location) if desired. For each location where system 100 is coupled with the spinal column, the system can be configured to slide superiorly and inferiorly to accommodate the patient's movement. Rigid rod connector 106 can be implanted directly through the interspinous ligament and can act as an anchor for the entire spinal correction system, preventing significant movement superiorly and inferiorly.

Sleeves 101 are configured so that they can be tunneled under the skin either on their own or with the help of a instrument inserted into the sleeve lumen. The sleeves are preferably configured to conform to the anatomy in the proximity of the spinous processes and surrounding tissue as they are advanced. The sleeves themselves preferably do not impart any corrective forces, but rather serve as guides for the rods that are placed through them. In an alternative embodiment, sleeves 101 are configured with a shape similar to that of the desired healthy spine. If iterative correction is applied, in order to prevent the need for removal of sleeves 101 during rod replacement, sleeves 101 are preferably flexible to a degree sufficient to accommodate rods 102 of varying shapes and sizes.

Upon attachment of corrective system 100, corrective force is applied to each vertebral body 11 lying adjacent to rods 102. The force is transmitted to each body 11 through the connection of the rods or sleeves directly to one or more vertebral bodies, as well as by the proximity of rods 102 with the spinous processes 14, the interspinous tissue 20 and/or the various other features of vertebral bodies 11 within the treatment region.

The use of an inferiorly and superiorly located sleeve on either side of the spinal column is also conducive to the use of multiple rod segments on both sides of the spinal column. For instance, rod 102-1 can include a first segment received within superiorly located sleeve 101-1 and a second, separate segment received within inferiorly located sleeve 101-3. Rigid rod connector 106 can be configured to couple the rod segments together as well as fix those segments with respect to rod 102-2 (or segments thereof) and the spinal column. The use of rod segments can facilitate the insertion procedure, as will be described in more detail below.

It should also be noted that a bundle of two or more rods or rod segments can be placed on either side of the spinal column. For instance, in one example embodiment, instead of a superiorly-placed rod segment on the left side of the spinal column, a bundle of three rod segments can be placed superiorly on the left side of the spinal column. These three rod segments can couple with a similar inferiorly-placed bundle of three rod segments, or a different number of inferiorly-placed rod segments can be used. Preferably, the bundle of rods or rod segments is banded or otherwise connected together and placed within a sleeve, although each rod or rod segment could be placed within its own sleeve, with the sleeves then being coupled together.

FIG. 2C is a perspective view depicting an exemplary embodiment of spinal correction system 100 having multiple rods 102 arranged in a bundle. FIG. 2C depicts the superiorly located portion of system 100 including sleeves 101-1 and 101-3. Sleeves 101-1 and 101-3 are shown to be transparent for ease of illustration of the components therein. FIG. 2D is a cross-sectional view taken along line 2D-2D of FIG. 2C.

Received within lumen 103-1 of sleeve 101-1 is a bundle of three rods 102-1, 102-2 and 102-3, which are held in relation to each other by coupling device 290-1. Similarly, received within lumen 103-3 of sleeve 101-3 is a bundle of three rods 102-4, 102-5 and 102-6, which are held in relation to each other by coupling device 290-3. Coupling devices 290 preferably allow rods 102 to slide within the respective lumens in coupling devices 290. A similar arrangement could be present in the inferiorly located portion of system 100 within sleeves 101-2 and 101-4. Fixed coupling device 106 is coupled with rods 102-3 and 102-6 of the two respective bundles. Each rod 102 can include a keyed portion to maintain the radial orientation of each rod with respect to the others. Here, the keyed portion is formed by a rib 291 located along the length of each rod. Ribs 291 are configured to interface with a complementarily shaped lumen within coupling devices 106 and 290.

This configuration of system 100 allows the medical professional to adjust the force applied while minimizing the effort necessary to remove portions and implant new portions of system 100. For instance, to lessen the force applied, the medical professional can simply remove a rod from each bundle. Rods 102-1, 102-2, 102-4 and 102-5 are each preferably only slidably received within coupling devices 290, making removal relatively simple. Rods 102-3 and 102-6 are preferably left in place to avoid the need to remove and reattach coupling device 106. Similarly, if an open lumen is present in coupling devices 290, a rod 102 can be added to increase the force applied. One of skill in the art will readily recognize that any number of rods can be used within each bundle.

FIG. 2E is a perspective cutaway view depicting another exemplary embodiment of rod 102. Here, rod 102 is configured with multiple components 141-143 to allow adjustment of the corrective force applied. FIG. 2F is a cross-sectional view of rod 102 taken along line 2F-2F of FIG. 2E. Included are an outer tubular component 141, an inner tubular component 142 and a central core component 143. Similar to the previous embodiment, this embodiment allows the applied corrective force to be adjusted with minimal effort during surgery. Outer tubular component 141 is preferably coupled with a similar component on the other side of the spinal column by way of a fixed coupling device (such as coupling device 106 described herein). Adjustment of the applied corrective force can be accomplished by modification of the components present. Preferably, the corrective force can be lessened by removal of inner tubular component 142 or core component 143. Likewise, force can be added through the addition of components. One of skill in the art will readily recognize that any number of components can be present.

Figure 2G:
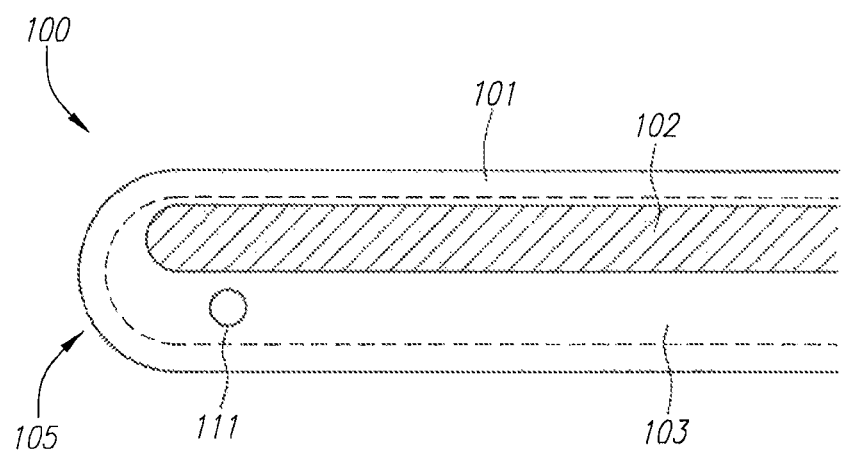
FIGS. 2G-H are cross-sectional views of additional exemplary embodiments of a spinal corrective system.

FIG. 2G is a cross-sectional view of an exemplary embodiment of corrective system 100 where tubular member 101 includes two through-holes 111 in opposing positions in the side wall through which a coupling device (e.g., coupling devices 108 or 109 described earlier) can be routed. Through-holes 111 can be offset to one side of tubular member 101 so as to not interfere with the movement or location of rod 102 within inner lumen 103.

Figure 2H:
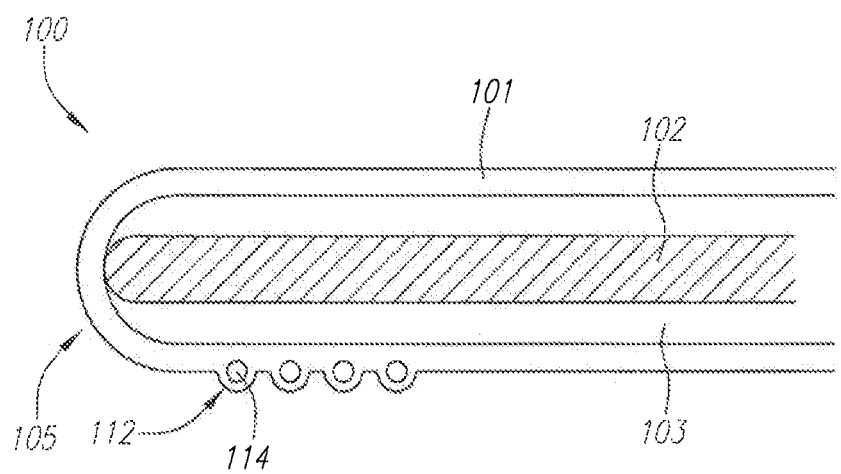

FIG. 2H is a cross-sectional view of another exemplary embodiment of corrective system 100 where tubular member 101 includes one or more (in this example four) raised portions 112 each having an aperture or through-hole 114. A coupling device (e.g., coupling device 108 or 109) can be routed through one or more of apertures 114 to couple tubular member 101 with another tubular member 101 (not shown) or with a portion of the patient's anatomy, such as spinous process 14 (also not shown).

The use of multiple raised portions provides the medical professional with optional locations on tubular member 101 to use for coupling. For example, the raised portion 112 located in the most suitable position for coupling to the spinous process can be selected. Alternatively, the medical professional can couple through more than one aperture 114 for added security or strength. For instance, a tether (e.g., braided wire) could be routed through each of apertures 114 to distribute the load in a relatively uniform fashion. Here, raised portions 112 are shown arranged in series longitudinally along the tubular member 101, although it should be understood that raised portions 112 can also be arranged radially about the circumference of tubular member 101, or any combination thereof. Also, instead of raised portions 112, tubular member 101 can include recessed portions having a strut or hook about which the coupling device can be routed, giving tubular member 101 an overall lower profile.

Figure 2J:
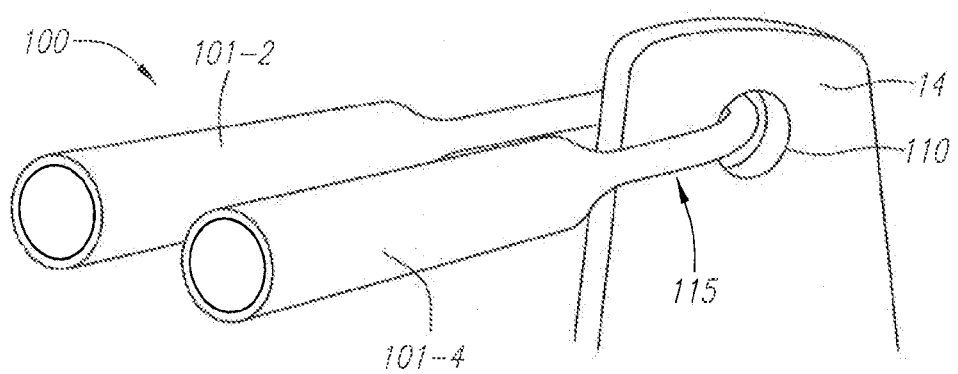
FIGS. 2I-J are perspective views of additional exemplary embodiments of a spinal correction system.
Figure 2I:
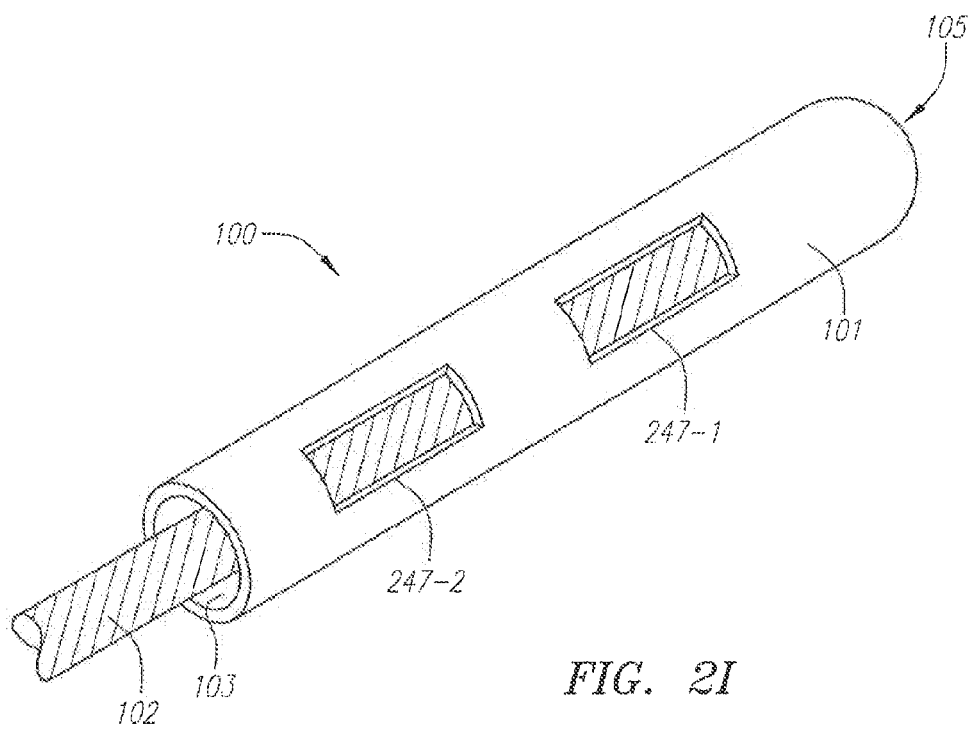

FIG. 2I is a perspective view of an exemplary embodiment of system 100 where sleeve 101 includes longitudinal slots, or cutouts, 247-1 and 247-2, which are configured to allow sleeve 101 and rod 102 to fit closely with the adjacent spinous processes. Here, only a portion of sleeve 101 is depicted. Slots 247-1 and 247-2 are positioned according to the location of the spinous processes of the portion of the patient's spinal column to be treated. Each spinous process is received within the respective slot 247, allowing rod 102 to be positioned relatively closer to the spinous process. This can be desirable in applications where close placement of rod 102 to the spinous process is desired for increased accuracy or precision in the application of the corrective force. Also, the close proximity of sleeves 101 and rods 102 to the surface of the vertebrae minimizes the stress placed on the attachment device. This embodiment of sleeve 101 is particularly suited to use with attachment devices such as those embodiments described with respect to FIGS. 5H-L, although not limited to such. It should be noted that instead of multiple slots 247, only one continuous slot can be present to more freely allow sleeve 101 to slide back and forth across spinous processes 14, if desired.

FIG. 2J is a perspective view of another exemplary embodiment of spinal correction system 100 where tubular members 101-2 and 101-4 are coupled together by connective portion 115, which is routed through iatrogenic opening 110 in spinous process 14. Here, a separate spinal coupling device (e.g., coupling device 109) can be omitted since the functionality is integrated into tubular members 101 themselves. To achieve the configuration depicted here, tubular members 101 are preferably flexible enough to allow distortion while the tubular member is passed or threaded through opening 110. The attachment to spinous process 14 preferably occurs at a superiorly located as an inferiorly located position. Again, sleeves 101 are preferably formed from a polymeric material such as polyethylene (PE), polyetheretherketone (PEEK), polytetrafluoroethylene, fluorinated ethylene/propylene copolymers, silicones, hydrogels, hydrophilic coatings, polyurethane (PU), and the like.

Although spinal correction system 100 preferably includes sleeves 101 for attachment to spinal column 10, it should be understood that rods 102 can be directly attached to spinal column 10 with the omission of sleeves 101 altogether. Embodiments of system 100 that attach to spinal column 10 without reliance on sleeves 101 are described in the parent U.S. patent application Ser. No. 11/656,314 and entitled "Orthosis to Correct Spinal Deformities," which is fully incorporated by reference herein.

It should be noted that any number of corrective systems 100 can be coupled to spinal column 10 at multiple locations along the length of spinal column 10. The use of multiple systems 100 allows relatively more localized correction. Different systems 100 can be configured to apply different degrees of corrective force in different directions and can be placed contiguously, or at spaced apart locations on spinal column 10 leaving vertebral bodies 11 to which no corrective force is applied. For example, if a spinal deformity bridged multiple regions (cervical and thoracic, thoracic and lumbar, all three regions, etc.) of the spinal column, then different systems 100 could each be targeted to treat those different regions of the spinal column.

The use of multiple systems 100 can allow greater freedom of movement to the patient. Also, in the case where the systems 100 are placed in a partially overlapping manner, less additional length of each sleeve 101 and rod 102 is required in the regions extending past the most superiorly and inferiorly located vertebral bodies to be treated since extra length needed to accommodate full range of motion and growth over time is distributed among the multiple systems 100. Also, corrective systems 100 can be made to overlap such that two sets of rods 102 can apply different amounts of corrective forces in different directions on the region of the spine in the overlapping portion. Furthermore, the use of multiple corrective systems 100 can facilitate implantation and replacement, depending on the anatomy and the desired strategy for correction. For instance, with multiple systems 100, replacement can be limited to only the necessary components to achieve the desired correction.

In addition, more than one rod can be used along a single side of the spinal column, either coupled directly to the spinal column or placed within or through a sleeve 101. FIG. 11 of the incorporated application Ser. No. 11/656,314 depicts an example of a multiple rod configuration where each rod is slidable with respect to the other. This allows two rods of varying stiffness to be used as well as allowing the rods to change length during flexion or extension of the patient's spine.

Figure 3A:
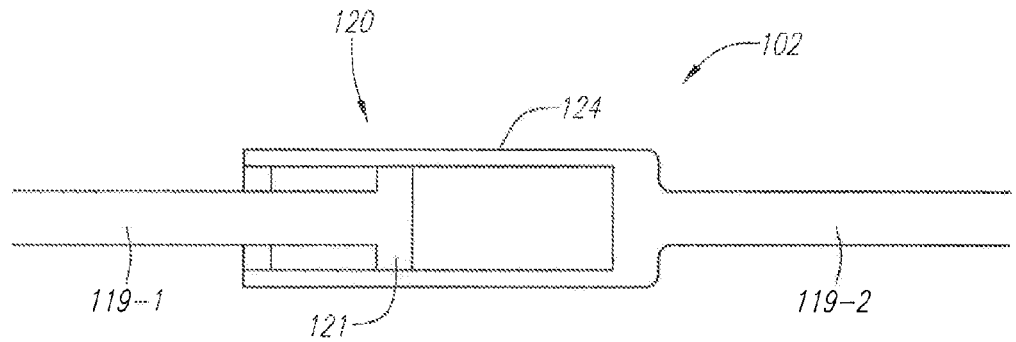
FIGS. 3A-B are cross-sectional views depicting exemplary embodiments of a rod for a spinal correction system.
Figure 3B:
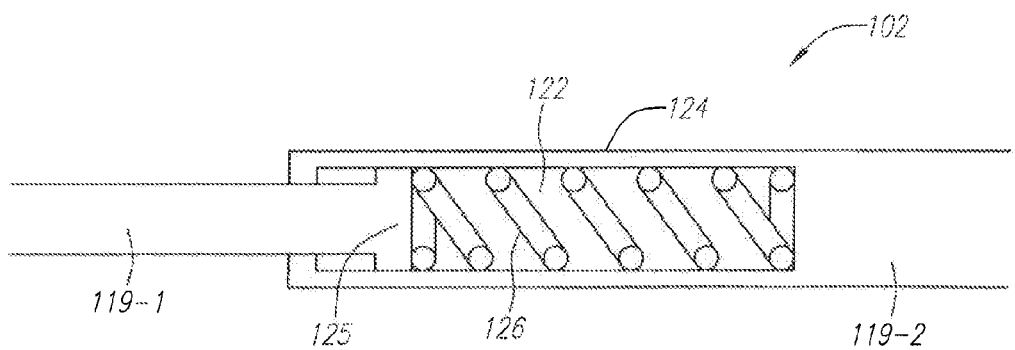

Alternatively, FIGS. 3A-B included herein depict an exemplary embodiment of a telescoping rod 102 for use in system 100. FIG. 3A is a cross-sectional view showing an exemplary embodiment of rod 102. Here, rod 102 includes a first rod segment 119-1 and a second rod segment 119-2 with a piston portion 120 located therebetween. Rod 119-2 includes a hollow portion having a side wall 124 configured to receive rod 119-1. The hollow portion has a sealing member 123, such as a gasket, that is configured to encompass rod 119-1 and guide its movement into the hollow portion. Rod 119-1 includes a sealing member 121 configured to compress the volume located within region 122 in a piston-like manner. Depending on the substance filling the volume of region 122, the amount of force necessary to compress rods 119-1 and 119-2 towards each other can be varied.

FIG. 3B is a cross-sectional view depicting another exemplary embodiment similar to that of FIG. 3A. Here, rod 119-1 has an enlarged end 125 that is configured to compress a bias element 126 located within chamber 122. In this embodiment, the volume within chamber 122 does not need to be compressed since the biasing is provided by bias element 126. Bias element 126 can be any compressible and expandable structure. Here, bias element 126 is configured as a spring.

Figure 3C:
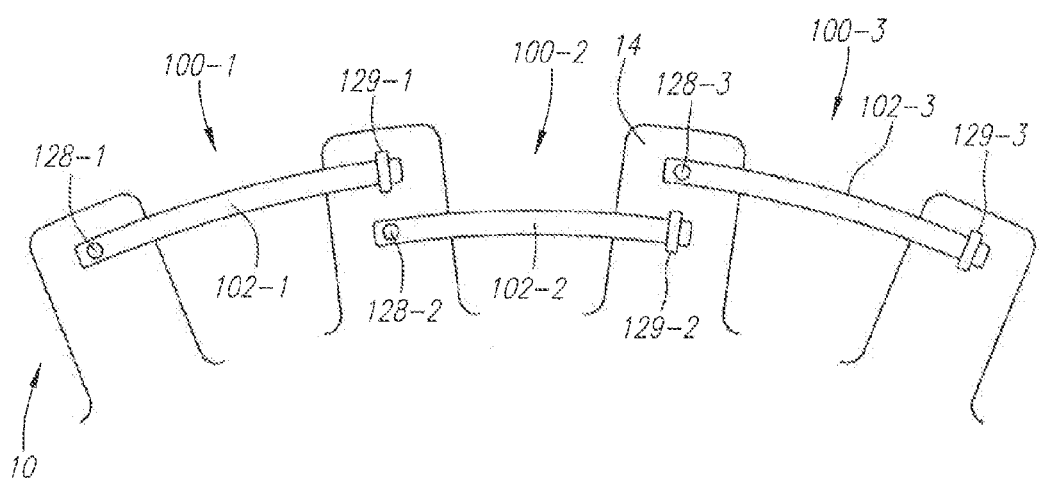
FIG. 3C depicts an exemplary embodiment where three spinal correction systems are coupled in series along patient's spinal column.

FIG. 3C shows an exemplary embodiment where three systems 100-1, 100-2 and 100-3, each having a rod 102-1, 102-2 and 102-3, respectively, are coupled in series along patient's spinal column 10. Here, spinal column 10 is shown in full flexion. Each rod 102 has a fixed connector 128 that fixedly connects the rod to a first spinous process 14. Each rod can also have one or more slidable connectors 129 to one or more adjacent spinous processes 14 (only one slidable connector 129 per rod 102 shown here). Slidable connector 129 allows rod 102 to slide in relation to the spinous process 14 to which the slidable connector 129 is attached. Exemplary slidable connectors are described herein as well as in the incorporated parent application.

Turning now to the attachment of spinal correction 100 to the spinal column, various methods and devices for attachment are disclosed in the incorporated parent application. These include U-shaped clamps that are fixedly screwed to the spinous process, such as that described with respect to FIG. 2 of the parent application. Also disclosed are opposing plate-like devices that are screwed through the spinous process and include textured or spiked surfaces that increase friction with the underlying bone, such as that described with respect to FIG. 5 of the parent application.

Additional attachment devices are provided herein having various configurations and methods of attachment. It should be noted that any of these devices can be fixedly screwed to the patient's spinal column and can take advantage of the use of textured surfaces or spiked surfaces such as described in the parent application. Accordingly, those structures and methods of attachment will not be repeated.

As will be discussed in more detail herein, attachment to the patient's spinal column preferably occurs in a minimally-invasive manner to limit the amount of exposure of each vertebral body attached to the spinal correction system. In a preferred embodiment, the spinous process is the only portion of those vertebral bodies in the region to be treated that is exposed during surgery. Preferably, no tissue anterior to the base of the spinous process is dissected and exposure of the laminae and facet joints is avoided. This can prevent undesirable secondary effects (e.g., excessive blood loss, scarring, autofusion).

In another embodiment, the spinous process is exposed without dissecting any portion of the ligamentum flavum coupled with the vertebral body to which the spinal correction system is coupled. In yet another embodiment, the spinous process is exposed without exposing any portion of each lamina anterior to the flaring transitional region of that lamina. While in yet another embodiment, only the portion of the spinous process posterior to the flaring transitions is exposed. Each of these embodiments will, among other things, reduce the scarring that will occur on or near the vertebral body of the patient. Accordingly, many of the embodiments of attachment devices described herein are configured to engage only the spinous process of each vertebral body, preferably, posterior to the flaring transitional regions of the spinous process and the laminae (although these devices can be configured to attach to other portions of the vertebral body if desired).

FIGS. 4A-B are perspective views of exemplary embodiments of an attachment device 201. Attachment device 201 can be used to couple any portion of corrective system 100 to the patient's spinal column 10, preferably the spinous process 14. For instance, attachment device 201 can be used to couple one or more of tubular members 101 or flexible rods 102 (neither shown) to spinous process 14. Also, attachment device 201 can be used to couple any other portion of corrective system 100 to spinous process 14, such as coupling devices 106, 108 or 109 (also not shown).

Here, attachment device 201 is generally U-shaped and includes a first plate-like side portion 202 and a second plate-like side portion 204 coupled together by an end portion 203. Plate-like side portions 202 an 204 oppose each other and are configured to attach to opposing sides of spinous process 14. In FIG. 4A, end portion 203 is placed over the posterior side 27 of spinous process 14 and in FIG. 4B, end portion 203 is placed over either the superior or inferior side of spinous process 14. Located on each plate-like side portion 202 and 204 is an engagement feature 205, which in this embodiment includes a raised portion 206 having a threaded lumen 207 therein. Engagement feature 205 can be configured in any manner desired to engage or interlock with the designated portion of spinal correction system 100 (e.g., sleeve 101, rod 102, coupling device 109, etc.).

Attachment device 201 can be attached to spinous process 14 using numerous different methods. For instance, attachment device 201 can be advanced over spinous process 14 and crimped onto spinous process 14 using a crimping tool. In this regard, attachment device 201 is preferably formed from a crimpable material such as nitinol, stainless steel, various rigid polymers and the like. Additional embodiments of attachment device 201 configured to be attached to the spinous process are described in FIGS. 5A-12B.

Attachment device 201 can also be configured to be self-adjusting to attach with spinous process 14, as will be described with respect to FIGS. 4C-E, 5A, 5D, 5F and 11A-D. FIGS. 4C-E depict an exemplary embodiment of attachment device 201 where plate-like portions 202 and 204 are biased towards each other. FIG. 4C is a top down view of this embodiment in an at-rest state where plate-like portions 202 and 204 are in close proximity to each other. Attachment device 201, in this embodiment, is preferably formed from an elastic material, such as spring steel, or a superelastic, shape memory material, such as nitinol, and biased towards the at-rest state depicted in FIG. 4C. In addition, attachment device 201 can be formed from a polymeric material with attached or integral metallic components configured to apply the bias.

Attachment device 201 can then be deformed or deflected from this at-rest state to an open state such as that depicted in the top down view of FIG. 4D. In this deflected state, attachment device 201 can be advanced over spinous process 14 and released. Once released, plate-like portions 202 and 204 deflect towards the at-rest state and exert a clamping force on spinous process 14 as depicted in FIG. 4E. Advancement and release of attachment device 201 can be facilitated with a delivery device (not shown).

Alternatively, attachment device 201 can be configured with thermally dependent shape memory characteristics. Configuration of nitinol to exhibit thermally dependent shape memory characteristics is well known in the art and will not be discussed herein. Generally, in such an embodiment, attachment device 201, at room temperature (or cooler), would be deformed to a state similar to that depicted in FIG. 4D and would exhibit only a minimal, if any, bias towards a separate state. Once in place over spinous process 14, attachment device 201 can be deformed to place plate-like portions 202 and 204 into contact with the opposing sides of spinous process 14. After implantation, the patient's body heats attachment device 201 and this heating activates the shape memory characteristics to cause attachment device 201 to exhibit a bias towards a state similar to that depicted in FIG. 4C, thereby causing attachment device 201 to clamp onto spinous process 14.

It should be noted that the use of adhesives, preferably quick-drying adhesives, can also be used to facilitate engagement of attachment device 212 to spinous process 14. In FIG. 4D, a quick-drying resin 208 is placed on the inner surface of plate-like portions 202 and 204. Adhesive 208 can be applied by the medical professional to the interior of plate-like portions 202 and 204 prior to the implantation procedure or can be pre-placed on portions 202 and 204 by a third party (e.g., the manufacturer). Alternatively, or in addition to placement on the inner surfaces of device 201, adhesive 208 can be applied to spinous process 14 by the medical professional prior to implantation of attachment device 201. A4

Figure 4F:
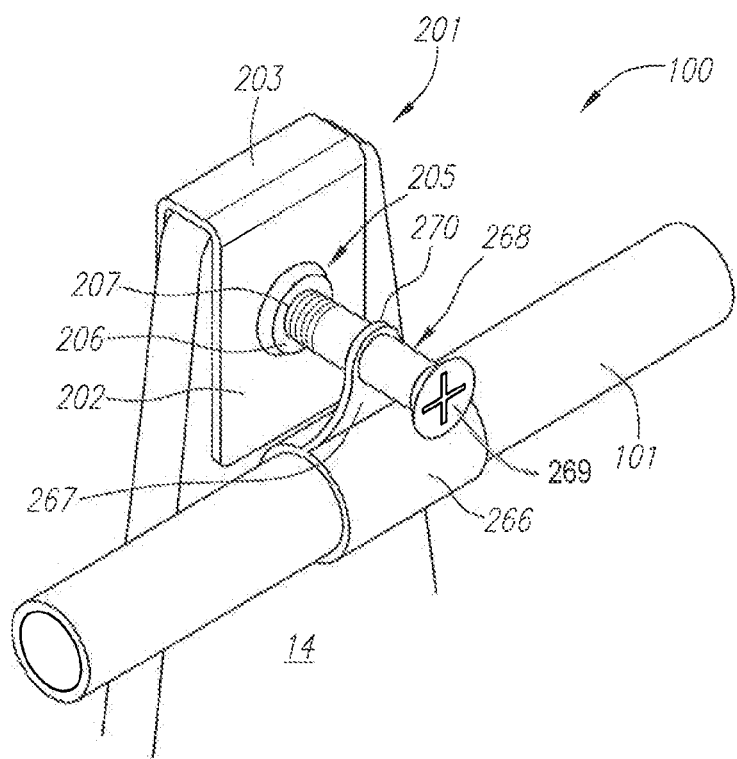
FIG. 4F is a perspective view depicting an exemplary embodiment of a spinal correction system implanted within a patient.

FIG. 4F is a perspective view of an exemplary embodiment of spinal correction system 100 attached to spinous process 14 by way of attachment device 201 and engagement feature 205 having threaded lumen 207. Here, sleeve 101 is received within an outer tubular member 266 which can be either slidably or fixedly coupled to an outwardly extending strut 267 having an aperture 270 therein. Aperture 270 is preferably aligned with lumen 207 in engagement feature 205 such that a screw 268 can be inserted through aperture 270 and into threaded lumen 207. Screw 268 is tightened until enlarged head portion 269 of screw 268 contacts strut 267 and provides the desired amount of fastening.

One of skill in the art will readily recognize, based on the description provided herein, that numerous types of engagement features 205 configured for many different types of attachment can be provided including, but not limited to, threaded (e.g., screw) features, latch features, snapable features, hookable features, crimpable features, clampable features, features for wired attachment, features to facilitate attachment with adhesives and the like.

In another exemplary embodiment, the surface of the spinous process can be modified to create recesses in which the attachment device 201 can be seated. For instance, with a U-shaped attachment device, a U-shaped chisel can be used to create grooves or slots on either face of the spinous process.

The grooves could be sized to receive the entire attachment device, or could complement keels or spikes on the inner surface of the portions 202 and 204. Portions 202 and 204 can then be tapped onto the spinous processes to anchor the keels or spikes into the grooves.

FIGS. 5A-F depict additional exemplary embodiments of attachment device 201 where device 201 is configured to surround the periphery of spinous process 14. One advantage of these configurations is that the devices 201 can be introduced laterally as opposed to posteriorly, which lessens the disruption and dissection of the interspinous ligament. An engagement feature 205 is shown on the near side of the spinous process 14 in FIGS. 5A-E, and can also be included on the opposite side as well. In the perspective view of FIG. 5A, attachment device 201 includes an elastic band 210 with a relatively more rigid section 211 thereon. Engagement feature 205 is located on rigid section 211, both of which can also be present on the opposite side of spinous process 14. Elastic band 210 is preferably composed of a biocompatible, polymeric material having sufficient life span to retain its structural integrity and elasticity over the duration of implantation, such as silicone or polyurethane, and the like.

Figure 5A:
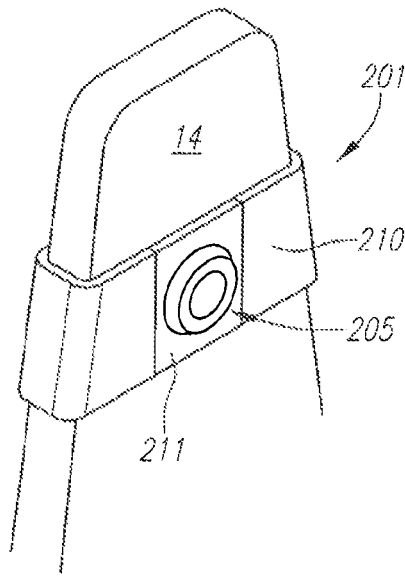
FIGS. 5A-E are perspective views depicting exemplary embodiments of attachment devices.
Figure 5B:
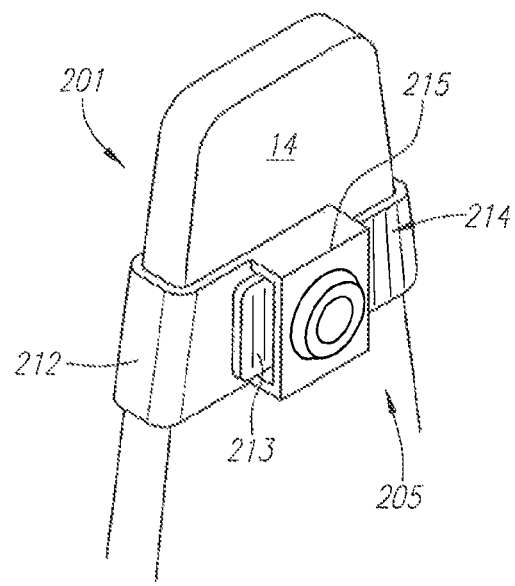

FIG. 5B is a perspective view of another exemplary embodiment of attachment device 201 where device 201 includes a strap-like member 212 having a first end 213 configured to slide into and be received by an opposing, second end 215 having a lumen therein. End 213 preferably includes engageable elements 214, which in this case are ribs or ridges in the surface of strap 212. Engageable elements 214 are preferably configured to interface with an opposing feature within end 215, such that a tightening motion is allowed, but the reverse motion (untightening) is prevented by the opposing features. The embodiment can operates in a "zip-tie" fashion, that is, the user advances end 213 through end 215, continually passing engageable elements 214 through end 215 until the desired tightness or compressive force is exerted, at which point reverse motion is prevented. Here, engagement feature 205 is located on the outer surface of end 215. Alternatively, strap 212 can be made of woven fibers made from polymers such as polytetrafluoroethylene (PTFE), polyethylene ptherethalate (PET) or ultrahigh molecular weight polyethylene (UHMWPE) or metal filaments such as nitinol, stainless steel, titanium alloys, and the like. The engageable element 215 could be configured as a buckle.

Figure 5C:
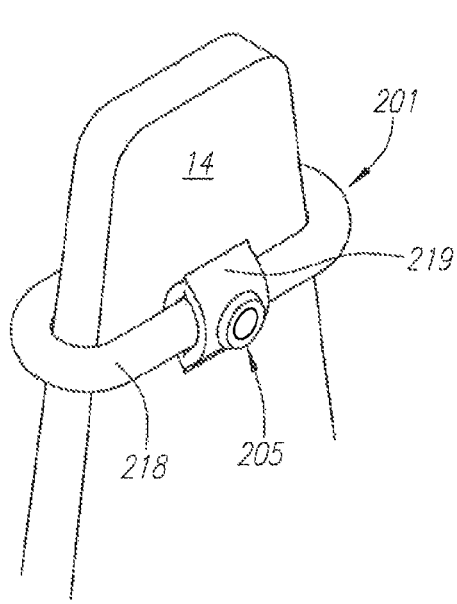

In the perspective view of FIG. 5C, attachment device 201 includes a flexible band 218 having opposing ends that are coupled together by a crimpable structure 219. Here, band 218 is placed over spinous process 14 with the desired amount of tension or compressive force, and crimpable structure 219 is then crimped over the ends to fasten them with relation to each other. Instead of a crimpable structure, a clamp, a snap or the like can also be used. In addition, self-tightening fasteners can be used. Alternatively, crimpable structure 219 can have two lumens to accommodate either end of the flexible band.

Figure 5D:
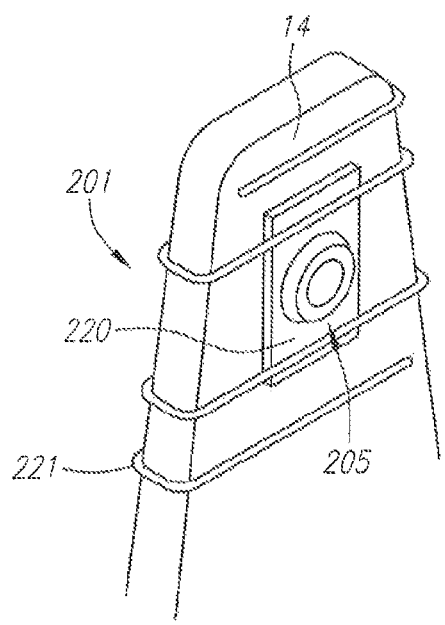

In the perspective view of FIG. 5D, engagement feature 205 is located on a plate-like base 220. Base 220 is maintained in place on spinous process 14 by a compressible coil 221. Adhesives can be used to facilitate the attachment of plate-like base 220 to spinous process 14 as well. Coil 221 is preferably deformed from a relatively smaller state around spinous process 14 such that it continues to exert a significant compressive force to hold plate-like base 220 in place. Base plate 2220 can also include features to facilitate attachment or placement of coil 221, such as eyelets, hooks, guides, recesses, and the like. Coil 221 can be formed from any elastic material including but not limited to nitinol, stainless steel, polymers, elgiloy, and the like.

Figure 5E:
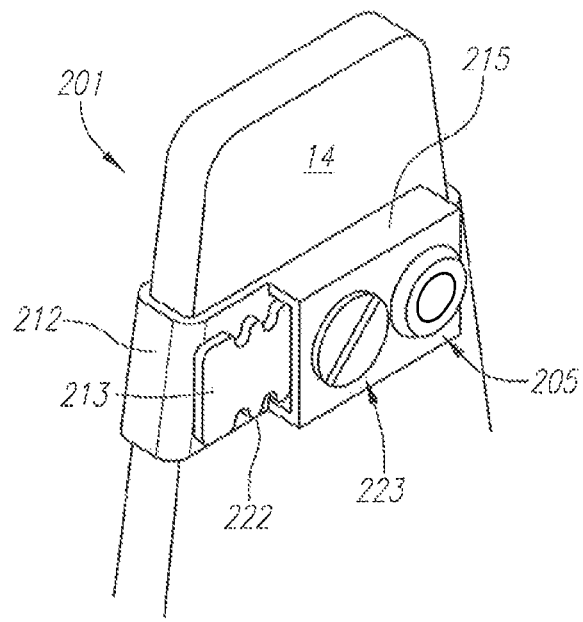

In the perspective view of FIG. 5E, attachment device 201 again includes a strap or band 212 having ends 213 and 215, with end 215 configured to receive end 213 within an inner lumen. End 213 preferably includes ridged or otherwise ratchetable elements 222 which are configured to operate with a ratchet 223 located on and within end 215. Here, ratchet (or screw drive) 223 is configured to be turned (either in a clockwise or counterclockwise fashion) to increase or decrease the tension on strap 212 by interfacing with ratchetable elements 222. Again, engagement feature 205 is located on end 215. In an alternative embodiment, attachment device 201 can be configured such that ratchetable elements 222 are grooves or holes in the center of band 212, as opposed to ridges on the edge of each band 212. In the embodiments of FIGS. 5B and 5E, an opposing engagement feature 205 can be placed directly on strap 212 on the opposite side of spinous process 14.

Figure 5F:
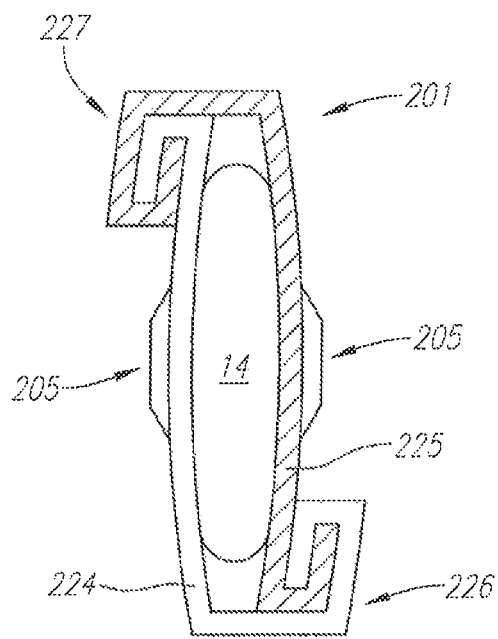
FIG. 5F is a posterior view depicting an exemplary embodiment of an attachment device.

FIG. 5F is a posterior view of another embodiment of attachment device 201 located on spinous process 14. Here, attachment device 201 includes two bodies 224 and 225, each having plate-like portions configured to oppose each other, as well as interlocking features 226 and 227 on the opposing ends. Here, each interlocking feature 226 and 227 is formed by complimentary hook-like features on each body 224 and 225. These features are preferably configured to maintain attachment device 201 in place over spinous process 14 by inducing deflection in bodies 224 and 225 to compress the spinous process 14 located therebetween. Alternatively, bodies 224 and 225 can be threaded or perforated at one end so compression is achieved by tightening a screw or other adjustable device disposed through both bodies 224 and 225.

Figure 5G:
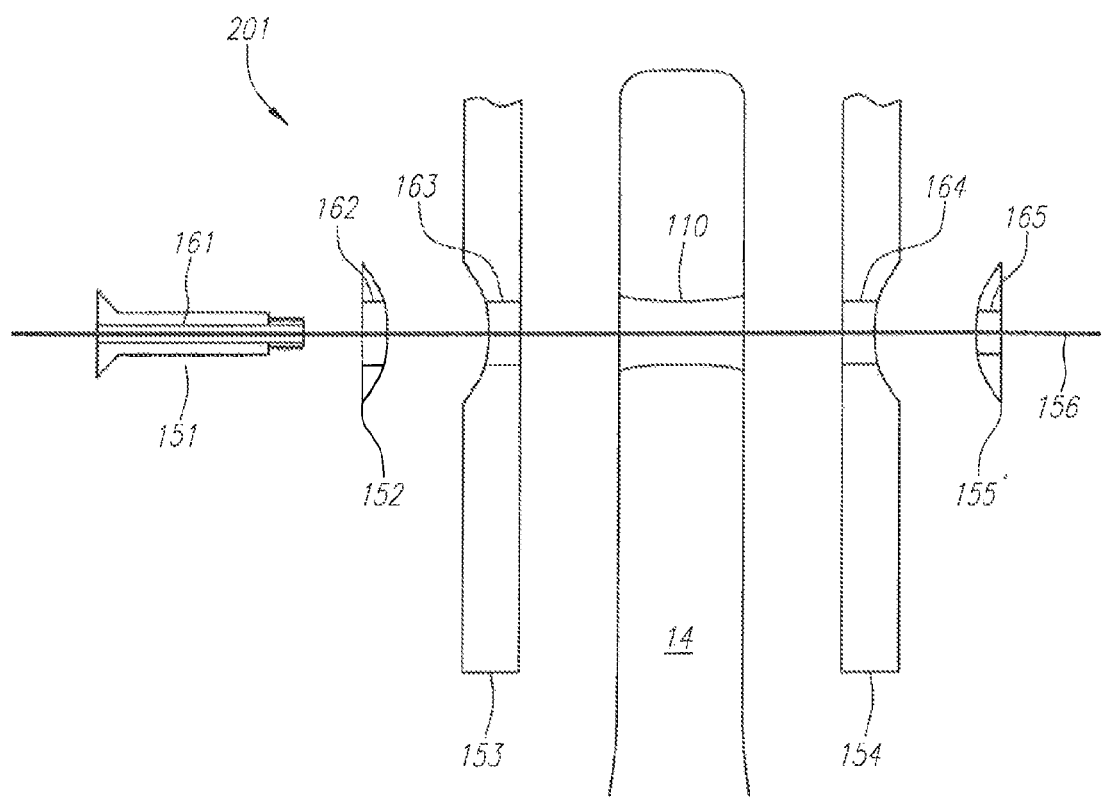
FIG. 5G is an exploded cross-sectional view depicting an exemplary embodiment of an attachment device and FIGS. 5H-L are perspective views depicting additional exemplary embodiments of attachment devices.

FIG. 5G is an exploded cross-sectional view depicting another exemplary embodiment of an attachment device 201, including cannulated elements configured to be positioned over a guidewire 156. Specifically, opposing plates 153 and 154, both having lumens 163 and 164, respectively, are positioned on opposing sides of spinous process 14, having iatrogenic opening 110, which in this embodiment need only be large enough o allow passage of guidewire 156 therethrough. Guide elements 152 and 155 have a washer-like configuration and are placed over plates 153 and 154, respectively, with the aid of guidewire 156. A coupling device 151, which is configured as a screw having lumen 161, is then advanced over guidewire 156 and through lumens 152 and 165 of guide elements 152 and 155, respectively. Lumens 162 and 165 are preferably configured to closely fit screw 151, which is also advanced through lumens 163 and 164 as well as opening 110. Lumen 165 of guide element 155 is preferably threaded to lockingly receive screw 151.

Guide elements 152 and 155 are preferably configured to allow angulation of screw 151 with respect to plates 153 and 154 when the components are routed over guidewire 156. In this embodiment, guide elements 152 and 155 have a convex surface configured to interface with a concave surface in each of plates 153 and 154, respectively, to permit variations in angulation, which can occur due to the variability in anatomy of spinous processes 14.

Alternatively, a variation of this embodiment can be used in the gap between adjacent spinous processes such that plates 153 and 154 compress against both sides of either or both of the superior and inferior spinous processes. Preferably, the width of coupling device 151 is small enough that it does not contact the opposing surfaces of the spinous processes above and below.

Figure 5H:
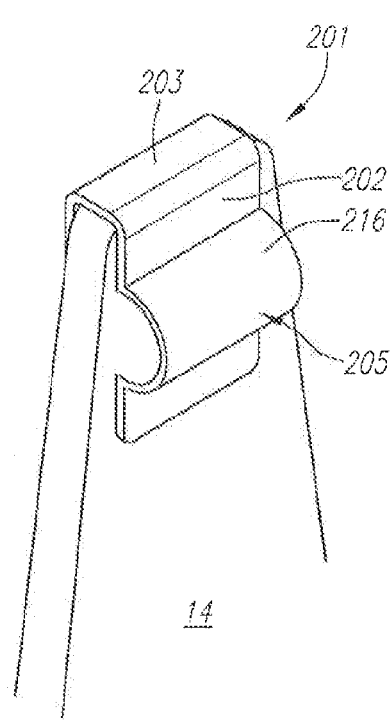
Figure 5I:
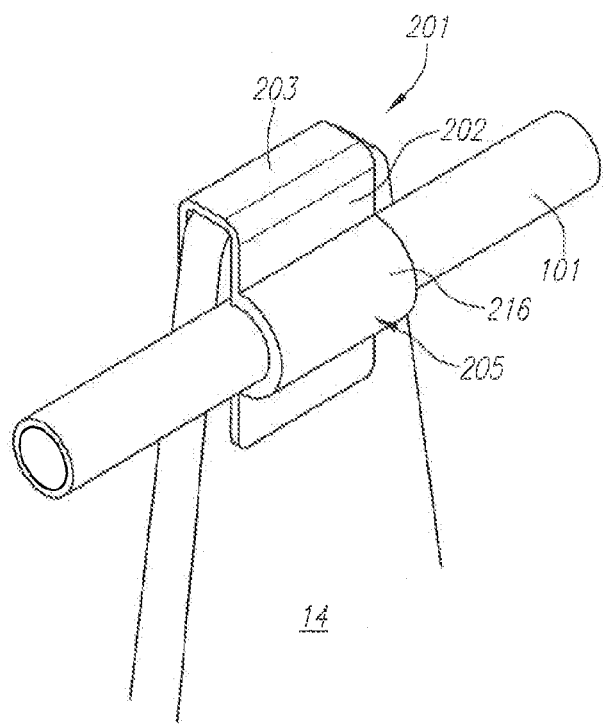
Figure 5J:
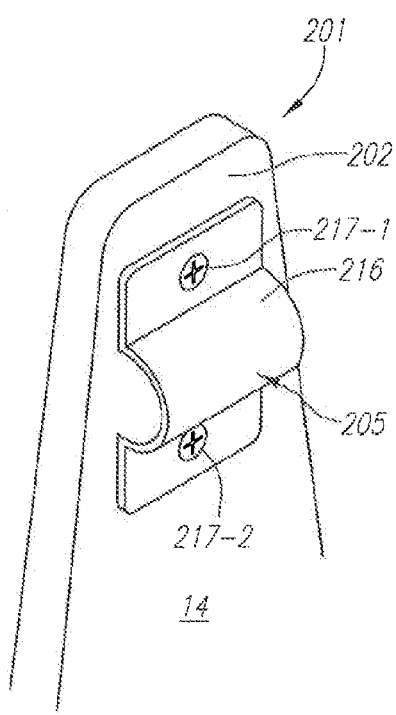
Figure 5K:
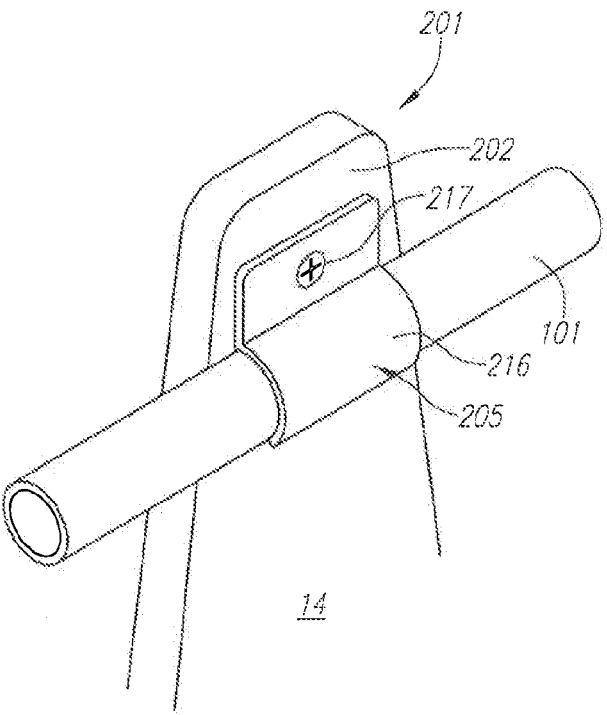

FIGS. 5H-L are perspective views depicting additional exemplary embodiments of attachment devices 201, where each embodiment allows sleeve 101 and/or rod 102 to be positioned relatively closer to the spinous process. FIG. 5H depicts an exemplary embodiment of attachment device 201 configured as a U-shaped clamp having an engagement feature 205 configured as a raised portion 216 offset from spinous process 14 to create a lumen therein. FIG. 5I depicts this embodiment with sleeve 101 contained beneath raised portion 216. FIG. 5J depicts a similar embodiment, except that attachment device 201 has a plate-like configuration and is fixed to spinous process 14 with screws 217-1 and 217-2. FIG. 5K depicts an exemplary embodiment where raised portion 216 only partially encompasses sleeve 101.

Figure 5L:
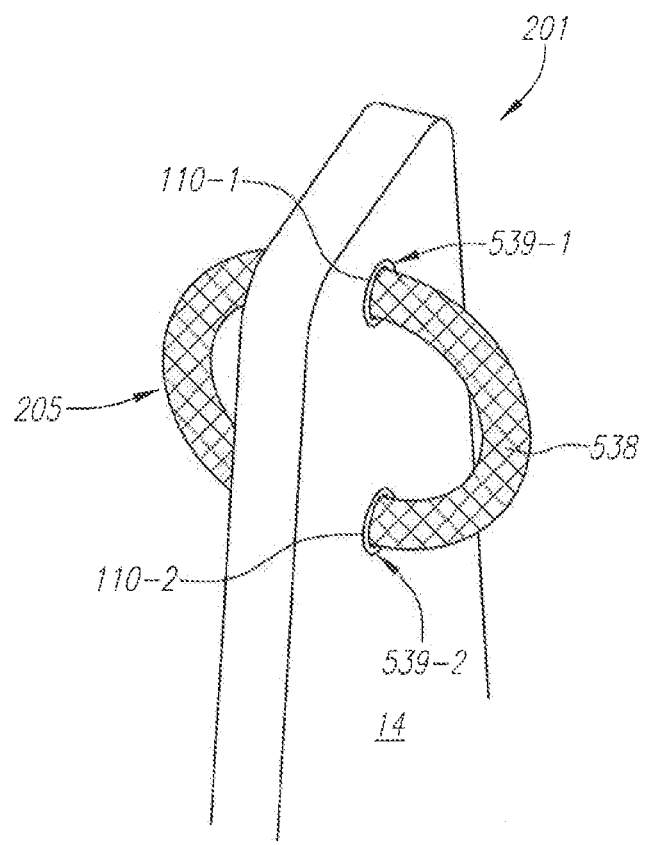

FIG. 5L depicts an exemplary embodiment where attachment device 201 includes an engagement feature 205 formed by a tether 538 routed through two iatrogenic openings 110-1 and 110-2 in the spinous process 14. Each iatrogenic opening 110-1 and 110-2 is lined by a grommet-like structure 539-1 and 539-2, respectively, to allow for reduced friction as tether 538 passes therethrough. Tether 538 can be a monofilament or a braided structure as shown here. Tether 538 is preferably formed from a biocompatible material including, but not limited to, nitinol, stainless steel, polymeric materials, and the like.

Figure 6A:
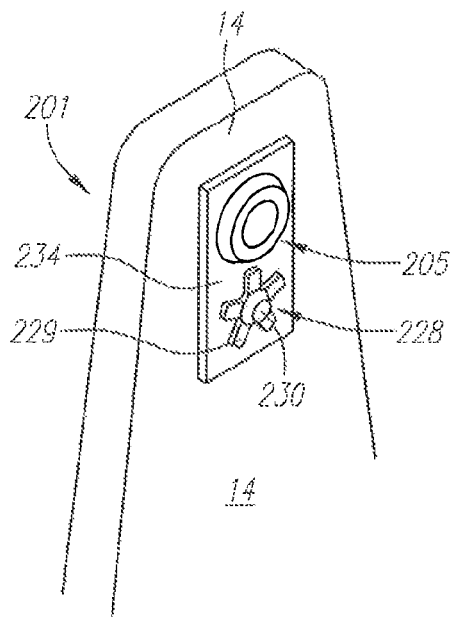
FIG. 6A is a perspective view depicting an exemplary embodiment of an attachment device.
Figure 6B:
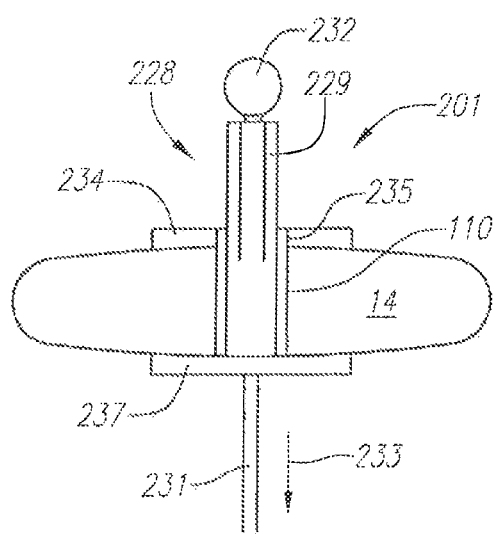
FIGS. 6B-C are cross-sectional views depicting stages of implantation of an exemplary embodiment of an attachment device.
Figure 6C:
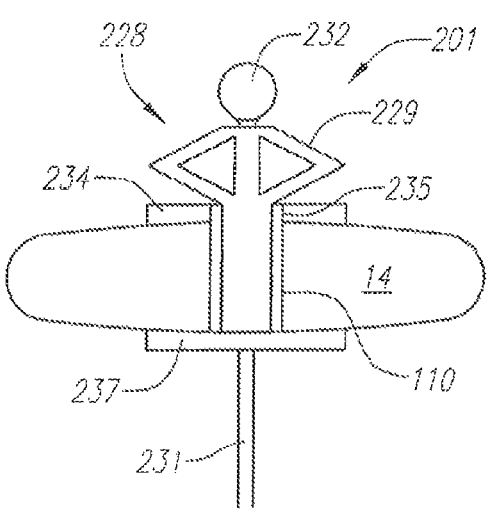

FIGS. 6A-C depict another exemplary embodiment of attachment device 201, where an expandable rivet-like structure is used to attach a plate-like base 234 to the spinous process 14. FIG. 6A is a perspective view showing an exemplary embodiment of expandable rivet 228 having a central lumen 230 and a plurality of bent struts 229 extending out over plate 234. FIGS. 6B-C are partial cross-sectional views showing a method of deployment of this embodiment of device 201.

An iatrogenic opening 110 in spinous process 14 is first formed to allow passage of device 201 therethrough. Attachment device 201 includes a second plate-like base 237 coupled with rivet 228 having a plurality of slots located therein, the portions of rivet 228 between slots forming struts 229. A pull rod 231 is placed within lumen 230 (not shown in FIGS. 6B-C). Pull rod 231 has an enlarged portion 232 at its distal end to abut with rivet 228. Base 234 has a lumen 235 and is placed over iatrogenic opening 10 with rivet 228 routed therethrough. Pull rod 231 is pulled proximally while applying a force on base 237 to maintain the apparatus in place.

The result is shown in FIG. 6C, where the proximal force has caused struts 229 to deflect outwards into a rivet-like configuration and engage base 234 thereby coupling base 234 and base 237 to the opposing sides of spinous process 14. Pull rod 231 can then be removed by advancing distally in a direction opposite to direction 233. Although not shown in FIGS. 6B-C, each base 234 and 237 preferably includes engagement feature 205 for coupling to corrective system 100.

In another embodiment, pull rod 231 can be omitted and rivet 228 can be expanded by applying compressive force to both sides of device 201 on process 14 with an externally located tool. In yet another exemplary embodiment, rivet-like structures 228 can be coupled on both sides of the spinous process. It should also be noted that this embodiment can be positioned in the space between adjacent spinous processes.

Figure 7D:
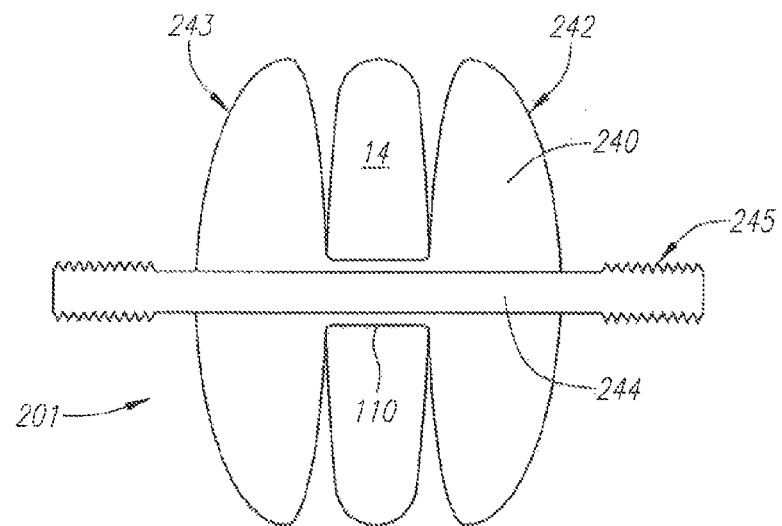
FIGS. 7D-E are cross-sectional views depicting exemplary embodiments of attachment devices.

FIGS. 7A-E depict additional exemplary embodiments of an attachment mechanism 201 for coupling with spinous process 14. FIG. 7A is a perspective view showing iatrogenic opening 110 through spinous process 14. An inflatable member 240, such as a flexible bag, balloon and the like, is provided with an optional inflation port 241. Balloon 240 is threaded through opening 110 as depicted in FIG. 7B. This can be performed manually or with the aid of a guidewire routed through opening 110. An inflation medium is then inserted into balloon 240 through inflation port 241. If no port is provided, the inflation medium can be injected directly through the wall of balloon 240. This inflation medium is preferably a cement or resin or other liquid that will harden over time, although gels and other viscous, semi-rigid, non-hardening materials can be used. Examples of suitable hardening substances include, but are not limited to, methylmethacrylate (MMA), polymethyl methacrylate (PMMA), epoxy resins, calcium phosphate, and the like.

Figure 7E:
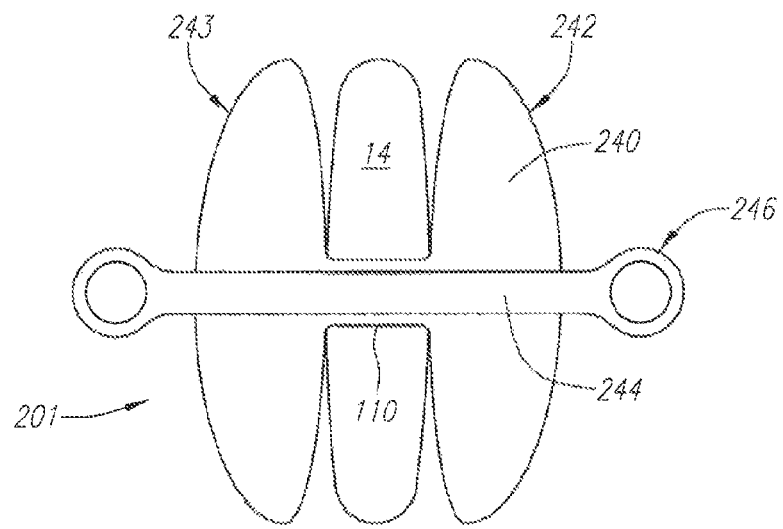

Once inflated, balloon 240 forms anchor portions 242 and 243 on opposite sides of spinous process 14 as depicted in FIG. 7C. These anchor portions 242 and 243 can then be relied upon as a basis for coupling to spinous process 14. Balloon 240, among other things, conforms to the surface profile of the spinous process 14, distributing force evenly and eliminating or reducing the potential of stress risers. FIGS. 7D-E are cross-sectional views depicting two exemplary embodiments of a through-rod 242 inserted through opening 110 and balloon 240. Through-rod 244 preferably includes engagement features on each opposing end to facilitate engagement of spinal correction system 100 to spinous process 14. Here, the engagement features of through-rod 244 are threaded portions 245 on either end (as depicted in FIG. 7B) or enlarged portions 246 having an eyelet (such as that depicted in FIG. 7E).

Through-rod 244 can be inserted into this configuration in several ways. Balloon 240 can be provided with a through-aperture (not shown) through which rod 244 can be inserted either before or after curing of the resin. If a through-aperture is present, it can also be used for threading balloon 240 through iatrogenic opening 110 prior to inflation. Alternatively, through-rod 244 can be inserted through balloon 240 and the resin therein prior to full curing of that resin. Or, after curing, a through-aperture can be drilled by the user to create the opening in which to insert through rod 244. Based on this description herein, one of skill in the art will readily recognize that there are other methods of inserting through-rod 244 that can also be used. Instead of inserting through-rod 244 after inflation, balloon 240 can have through-rod coupled thereto prior to threading through opening 110.

Figure 8A:
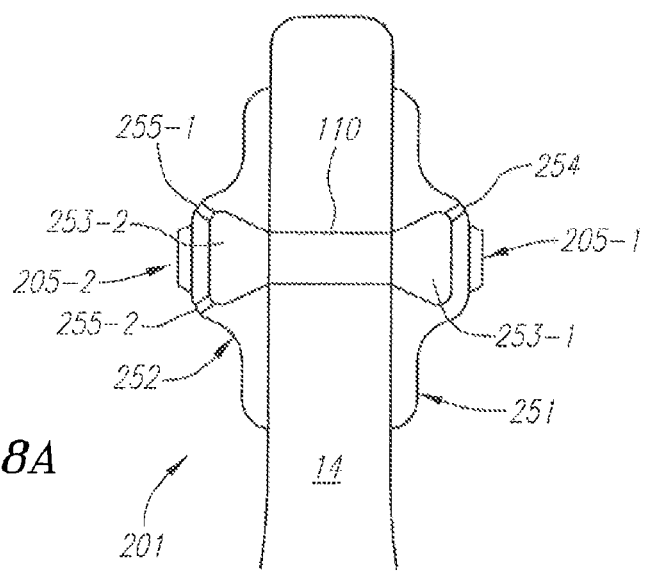
FIGS. 8A-B are cross-sectional views depicting stages of implantation of an exemplary embodiment of an attachment device.
Figure 8B:
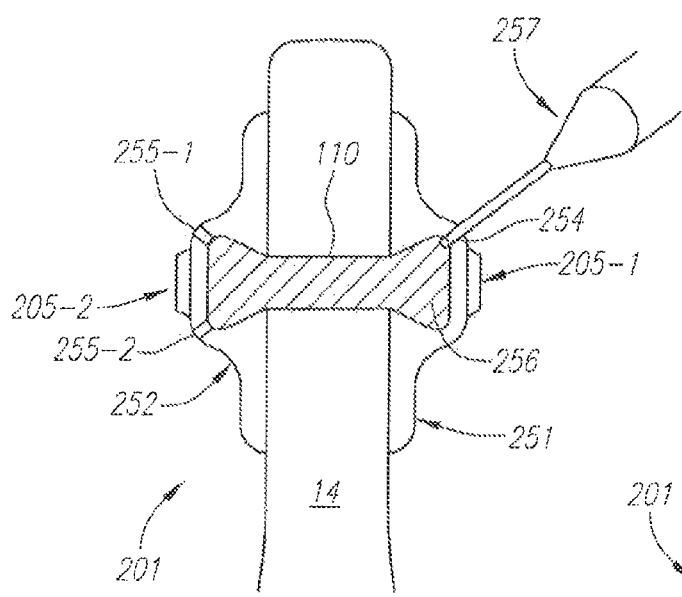

FIGS. 8A-B are cross-sectional views depicting another exemplary embodiment of attachment device 201, where attachment is made by filling iatrogenic opening 110 with a cement or resin. Preferably, this embodiment of device 201 includes a first side plate 251 and a second side plate 252 configured to interface with opposing sides of spinous process 14. Each plate 251 and 252 includes an internal chamber 253, which is preferably configured to form an anchor once filled with the cement or resin. Here, chamber 253 has a width that is tapered or stepped to provide resistance to detachment once filled with the cement or resin.

Plate 251 preferably includes an injection port 254 which communicates with chamber 253-1. Chamber 253-1 has an open end which is alignable with iatrogenic opening 110. Likewise, plate 252 includes an inner chamber 253-2 with an opening that is alignable with iatrogenic opening 110. Plate 252 also includes one or more (in this example, two) vent holes 255 that allow venting during injection of the cement or resin. Both plates 251 and 252 can include one or more engagement features 205 as well.

FIG. 8B depicts engagement device 201 after injection of resin 256 into chamber 253-1, opening 110 and chamber 253-2 by an injector 257. Injector 257 can then be removed. Plates 251 and 252 are preferably held in place until the cement or resin has cured sufficiently to lock plates 251 and 252 in place on spinous process 14. Again, examples of cements or resins can include methyl methacrylate (MMA), polymethyl methacrylate (PMMA), epoxy resins, calcium phosphate, and the like.

Figure 9:
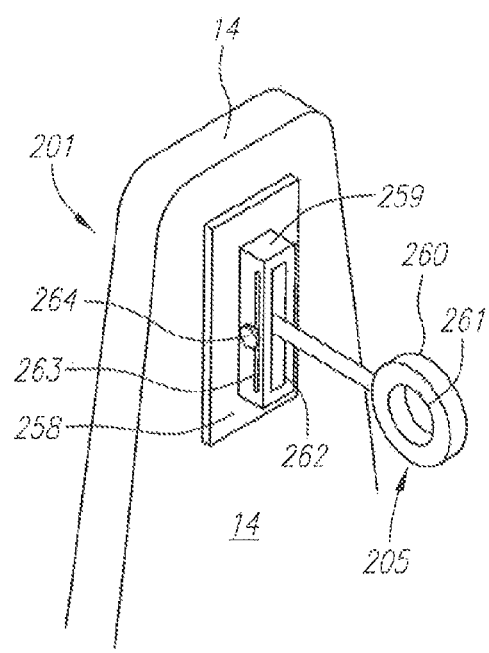
FIG. 9 is a perspective view depicting an exemplary embodiment of an attachment device.

FIG. 9 is a perspective view of another exemplary embodiment of attachment device 201 where the position of engagement feature 205 is adjustable. Here, adjustability is provided posteriorly and anteriorly (up and down as depicted here), but superior and inferior adjustment can also be provided as well as height adjustment from the surface of spinous process 14. Attachment device 201 includes a base 258 coupled with spinous process 14.

Base 258 preferably includes a housing 259 in which an elongate member 260 is connected and allowed to slide both posteriorly and anteriorly. Elongate member 260 includes an eyelet 261 for receiving rod 102 (not shown). It should be understood that elongate structure 260 can take any configuration and be configured to couple with any portion of corrective system 100, not limited to rod 102.

Once properly positioned, elongate structure 260 is fastened in place by a fastening device, such as set screw 264, which, in this embodiment, is allowed to slide with structure 260 through slot 263 in the side of housing 259. The ability to adjust position in this manner is beneficial in that it allows for more precise coupling of the spinal correction system 100 to the vertebral bodies 11. Small changes in position can lead to the exertion of large forces over the spinal column in the anterior and posterior directions. These forces can be significant in the case of segmental fixation, where every vertebral body in the treated region is coupled directly with the spinal correction system 100. These forces are generally undesirable since they are not corrective and can lead to different spinal deformities and potentially spinal stenosis. Thus, in these and other applications, position adjustability can be highly desirable.

Alternatively, elongate structure 260 can be allowed to freely slide (i.e., without fastening by set screw 264) according to forces through natural motion of the spinal column. It should be noted that base 258 can be configured and coupled with spinous process 14 in any manner including each of those described herein with respect to FIGS. 4A-8B and 10A-12B.

Figure 10A:
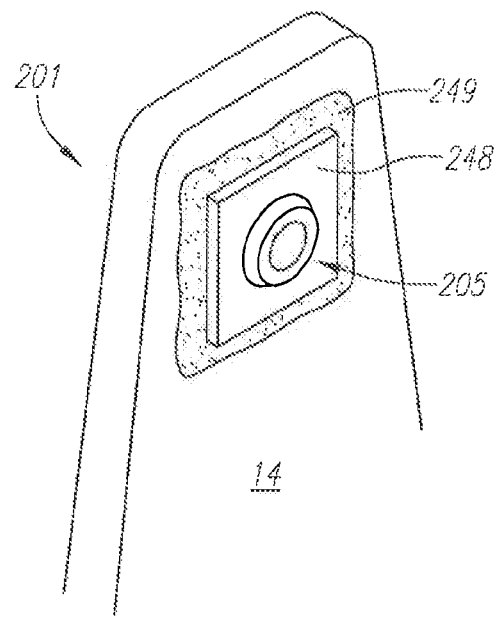
FIGS. 10A-B are perspective views depicting stages of implantation of an exemplary embodiment of an attachment device.

FIG. 10A is a perspective view depicting another exemplary embodiment of attachment device 201 where device 201 includes a plate-like, base structure 248 having an engagement feature 205 located thereon. Base 248 is coupled with spinous process 14 by way of a moldable material 249. Material 249 is preferably configured to harden over time and can be methyl methacrylate (MMA), polymethyl methacrylate (PMMA), epoxy resins, calcium phosphate, and the like.

Figure 10B:
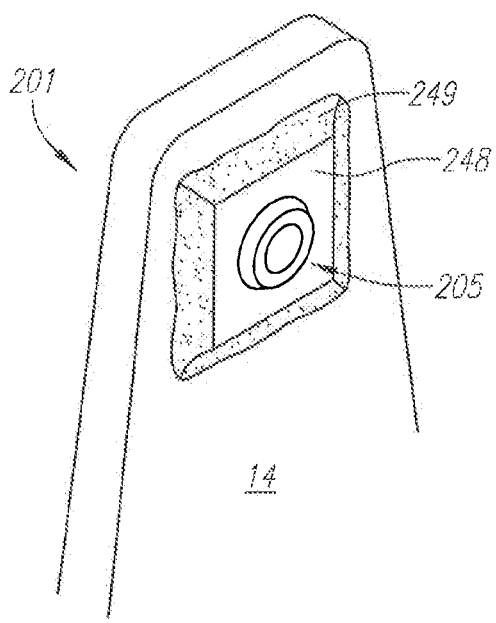

The use of moldable material 249 provides, among others, the ability to manually form material 249 around base 248 to provide a smooth, relatively atraumatic profile and limit any inflammatory response by the body. FIG. 10B depicts base 248 after placement on moldable material 249 and the forming, or molding, of material 249 around base 248 to provide a relatively atraumatic profile. Moldable material 249 can also be fed or forced into one or more iatrogenic recesses or through-openings in spinous process to increase the anchoring with the spinous process.

Figures 11A, 11B:
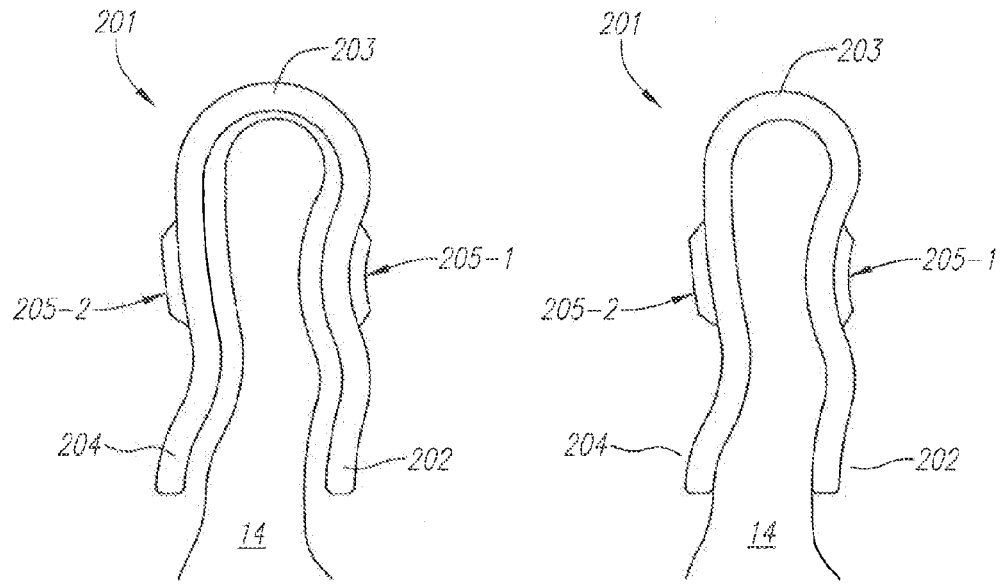
FIGS. 11A-D are cross-sectional views depicting stages of implantation of exemplary embodiments of attachment devices.

It is also possible to configure attachment device 201 to conform to the anatomy of the patient. For instance, FIGS. 11A-B depict an exemplary embodiment of attachment device 201 that has been customized for a certain patient's spinous process 14. Here, attachment device 201 has a U-shape (although it is not limited to such) with first side 202 and second side 204 both having different shaped configurations designed to complement and conform to the features on the patient's spinous process 14.

FIG. 11A depicts attachment device 201 just prior to being clamped on the spinous process 14 and FIG. 11B depicts attachment device 201 after attachment. Mapping data as to the features of the spinous process 14 can be obtained prior to surgery using any visualization method (e.g., CT scans, MRI and the like). The data can also be obtained during surgery using instruments such as a laser profilometer. The mapping data can then be used to manufacture portions 202 and 204 to complement the anatomy. The mapping data can also be used to manufacture any portion of system 100 to fit the patient's anatomy in a customized fashion.

Figures 11C, 11D:
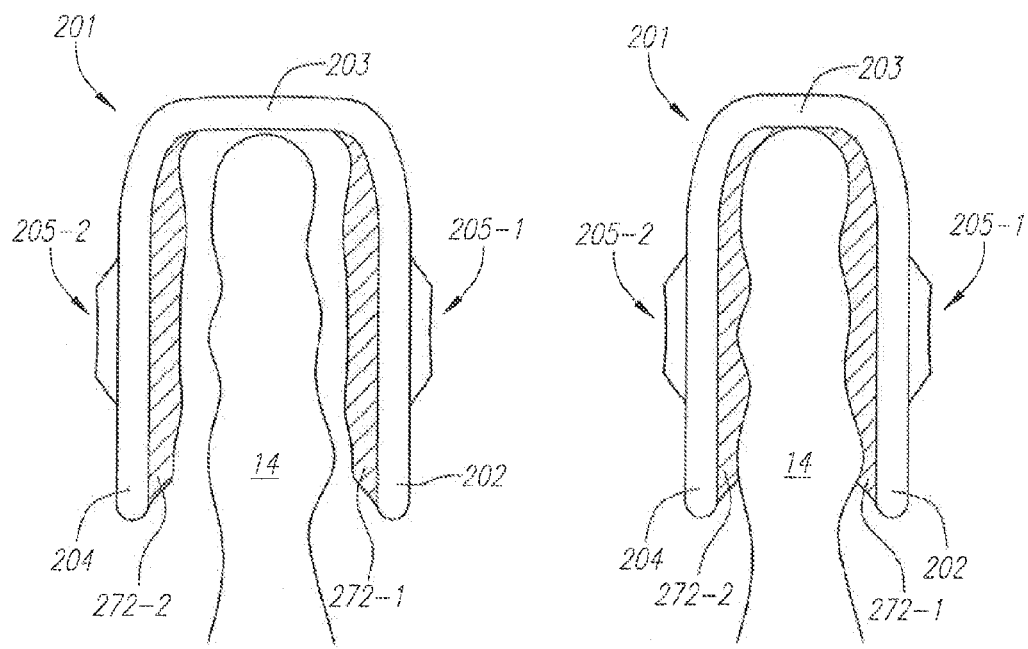

FIGS. 11C-D depict another exemplary embodiment of attachment device 201 where a compliant, or conforming, material 272 is coupled to the inner surface of first portion 202 and second portion 204. Compliant material 272 preferably conforms to the shape of the patient's spinous process when attachment device 201 is attached (FIG. 11C depicts attachment device 201 prior to attachment and FIG. 11D depicts attachment device 201 post-attachment). Compliant material 272 can be formed from any suitable material including, but not limited to, polymers, gels, rubbers, elastics, silicones and the like.

Figure 12A:
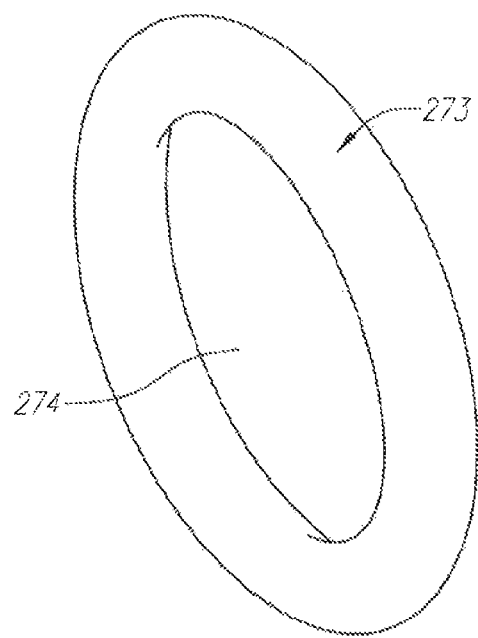
FIG. 12A is a perspective view depicting an exemplary embodiment of a toroidal element.

FIG. 12A depicts an exemplary embodiment of a compliant toroidal element 273 having an inner aperture 274. Toroidal element 273 is preferably placed over spinous process 14 during attachment of device 201 and acts, similar to material 272 described with respect to FIGS. 11C-D, to conform to the features of spinous process 14. Toroidal element 273 can be formed from a compliant material such as those described with respect to FIGS. 11C-D, or can be configured as a fillable structure (e.g., balloon, bag, sheath and the like) that is placed between plate 275 (or 277) and spinous process 14 and then filled with a biocompatible liquid or gel, or a hardening resin such as epoxy or methyl methacrylate (MMA).

Figure 12B:
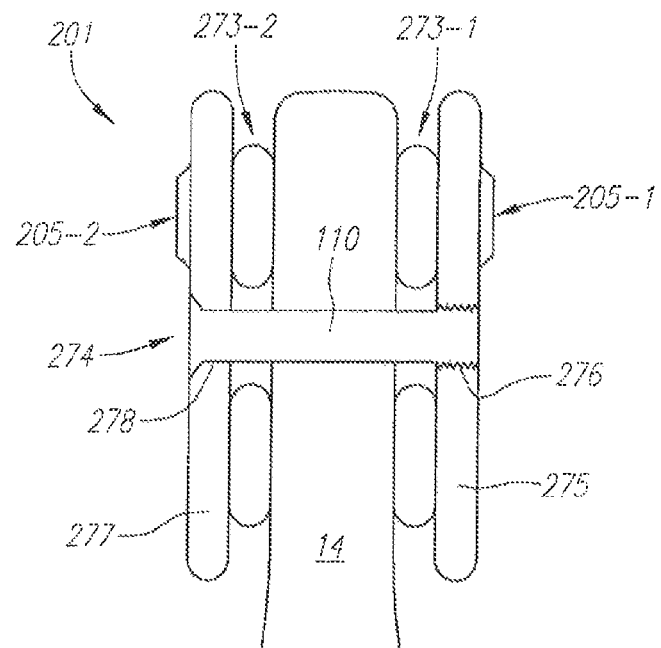
FIG. 12B is a cross-sectional view depicting an exemplary embodiment of an attachment device.

FIG. 12B is a planar cross-sectional view showing attachment device 201 in position over spinous process 14. Here, attachment device 201 includes first and second toroidal elements 273-1 and 273-2 located between spinous process 14 and opposing plates 275 and 277, respectively. Plate 275 includes a threaded lumen 276 for receiving a screw 279 which is inserted through lumen 278 in plate 277 and iatrogenic opening 110 in spinous process 14.

Based on the description provided herein, one of skill in the art will readily recognize that the compliant elements (e.g., 272 and 273) can be configured in other, non-toroidal manners to allow conformance of attachment device 201 to spinous process 14. Use of a moldable, compliant material allows for relatively standardized rigid attachment structures to be used without the need to pre-profile the patient's anatomy.

Figure 12C:
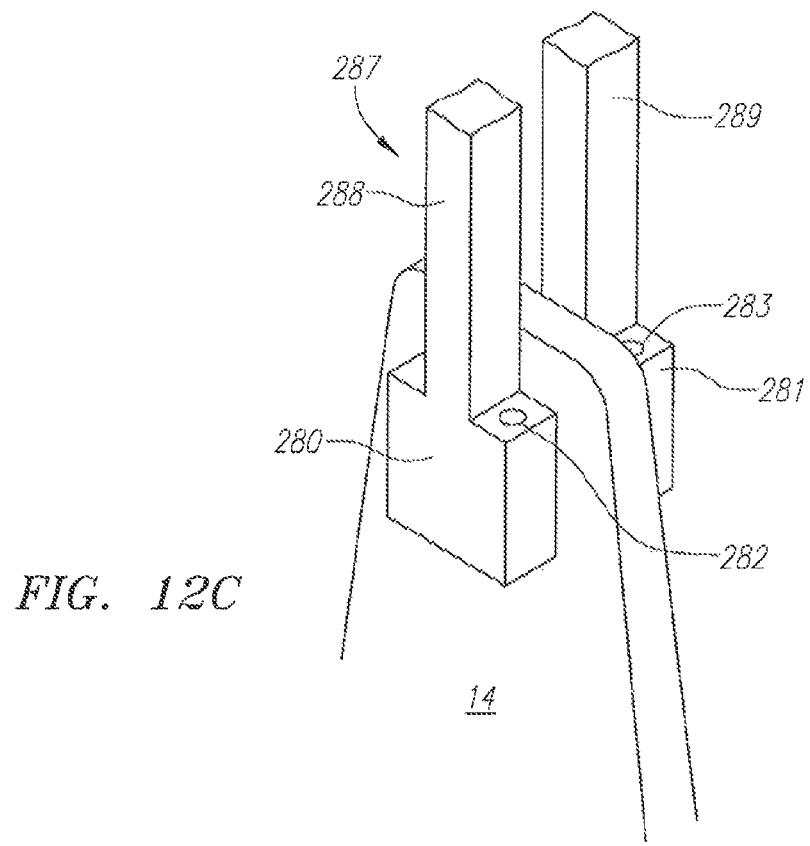
FIGS. 12C-D are perspective views depicting exemplary stages of casting an exemplary embodiment of an attachment device.
Figure 12D:
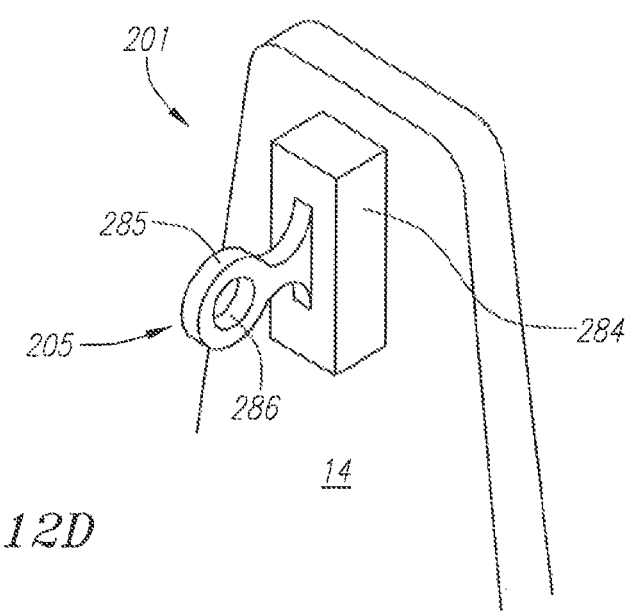

In addition to using prefabricated structures, attachment device 201 (or any portion thereof) can be cast in place over spinous process 14 during surgery. FIGS. 12C-D are perspective views depicting an exemplary embodiment of attachment device 201 during casting over spinous process 14. In FIG. 12C, a casting device 287, having two molds 280 and 281 coupled with shafts 288 and 289, respectively, are placed on opposing sides of spinous process 14 over an iatrogenic opening (not shown) extending therebetween. Mold 280 includes an injection port 282 through which the material to be cast is injected, and mold 281 preferably includes a vent port 283 for venting during the injection of the cement or resin. In an alternative embodiment, the cement or resin can be injected into mold 280 through an inner lumen in shaft 288. Venting can also occur through a lumen in shaft 289.

The inner surface of each mold 280 and 281 is shaped so as to cast the desired attachment device configuration, an example of which is depicted in FIG. 12D. Here, attachment device 201 includes a plate-like base 284 with an elongate strut 285 extending therefrom having an eyelet 286 through which a rod, sleeve spinal coupling device or any other component of the spinal correction system can be routed. A corresponding structure is preferably cast on the opposing side, the two opposing structures being fastened to each other and spinous process 14 by the presence of the resin or cement within the iatrogenic opening (not shown) in spinous process 14.

Like the embodiments described with respect to FIGS. 7A-E, the use of materials or configurations that conform to or match the shape of the patient's spinous process, such as in the embodiments described with respect to FIGS. 10-12D, provide for, among other things, the distribution of force evenly across the engaged surface and the elimination or reduction of the potential of stress risers.

Numerous embodiments of attachment devices 201 have been described, such as with respect to FIGS. 4A-12D. One of skill in the art will readily recognize that the features of those embodiments can be substituted for or combined with the features of any other embodiment. For instance, various techniques and configurations for attaching device 201 to the spinous process 14 are disclosed, and those techniques and/or configurations can be used in place of or in combination with any other technique or configuration disclosed.

As discussed earlier, provided herein are methods for minimally invasive implantation of spinal correction systems within the body of a patient. Preferably, the spinal correction system is attached to a spinous process of a patient's vertebral body by exposure of only the spinous process of that vertebral body, although other variations of minimally invasive implantation procedures have been described herein.

Figure 13:
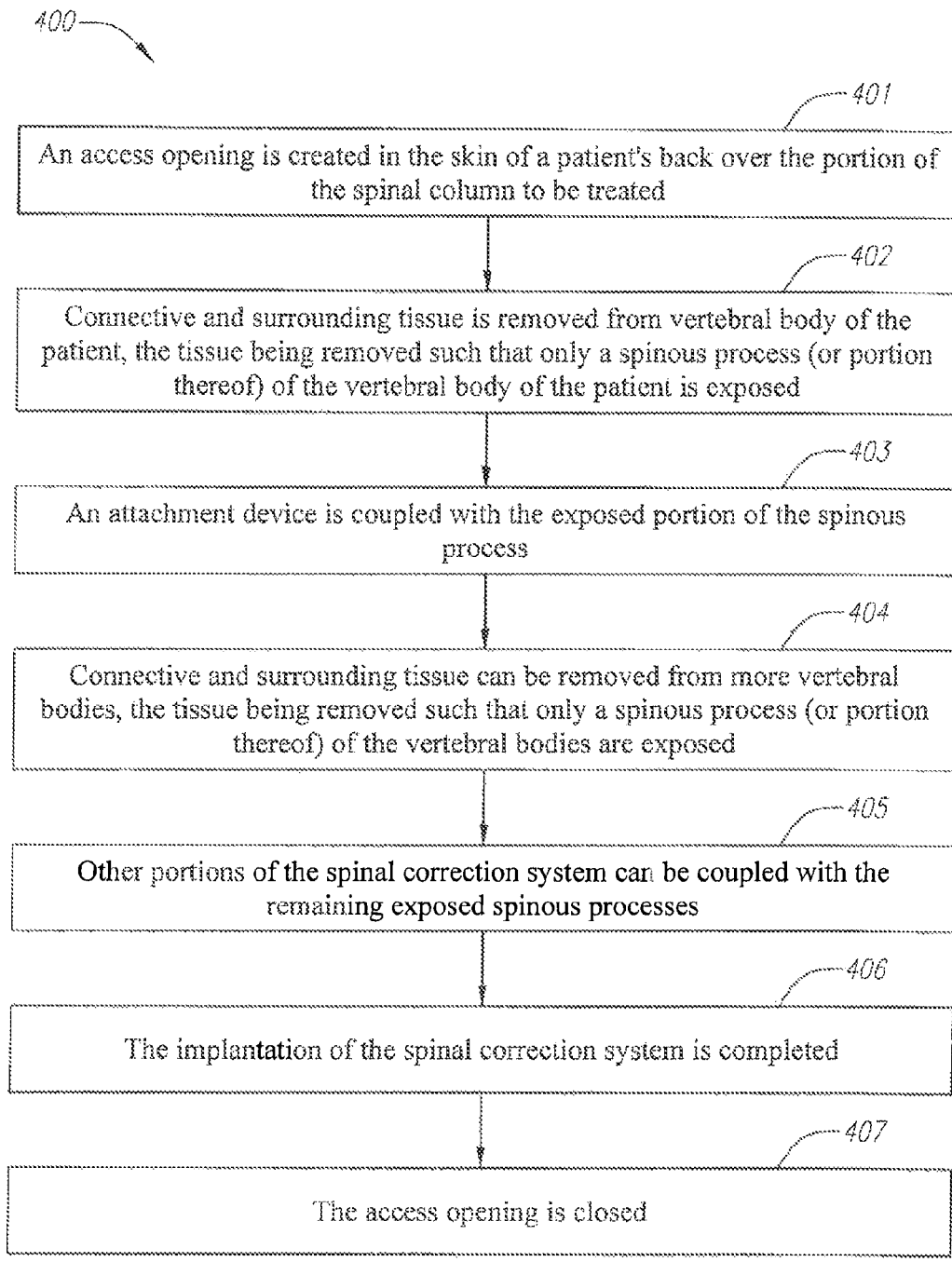
FIGS. 13-14 are flow charts depicting exemplary methods of implantation of a spinal correction system.

FIG. 13 is a flow chart depicting an exemplary method of implantation 400 of a spinal correction system in a minimally invasive manner. In this embodiment, only the spinous process of the vertebral bodies is exposed, but it should be noted that, in other embodiments of this method, different amounts of the vertebral body can be exposed, or tissue dissected therefrom, including each of the variations of the minimally invasive methods described herein.

At 401, an access opening is created in the skin of a patient's back over the portion of the spinal column to be treated. At 402, connective and surrounding tissue is removed from a vertebral body of the patient, the tissue being removed such that only a spinous process (or portion thereof) of the vertebral body of the patient is exposed. At 403, an attachment device is coupled with the exposed portion of the spinous process. The attachment device is preferably configured to allow the transmission of a corrective force from at least one elongate rod of the spinal correction system to the patient's spinal column. At 404, connective tissue can be removed from more vertebral bodies, if desired, preferably occurring such that only the spinous process (or a portion thereof) of the additional vertebral bodies is exposed. Once exposed, at 405, other portions of the spinal correction system can be coupled with those spinous processes. At 406, the implantation of the spinal correction system is completed and, at 407, the access opening is closed.

In removing the connective tissue from the spinous process of a patient's vertebral body, preferably, the medical professional will first gain access to the supraspinous ligament and create an incision through that ligament to gain access to the underlying interspinous tissue. In this embodiment, any tissue connected with the spinous process is then dissected from the spinous process, taking care to avoid dissection from, at least, the anterior portion of the flared transitional regions, and preferably the entirety of the transitional regions. As noted above, preferably the facet joints and the laminae are left unexposed as well. The dissected tissue can include connective tissue such as the interspinous ligament as well as surrounding muscular or fatty tissue. The dissected tissue is pulled away to expose the spinous process.

Figure 14:
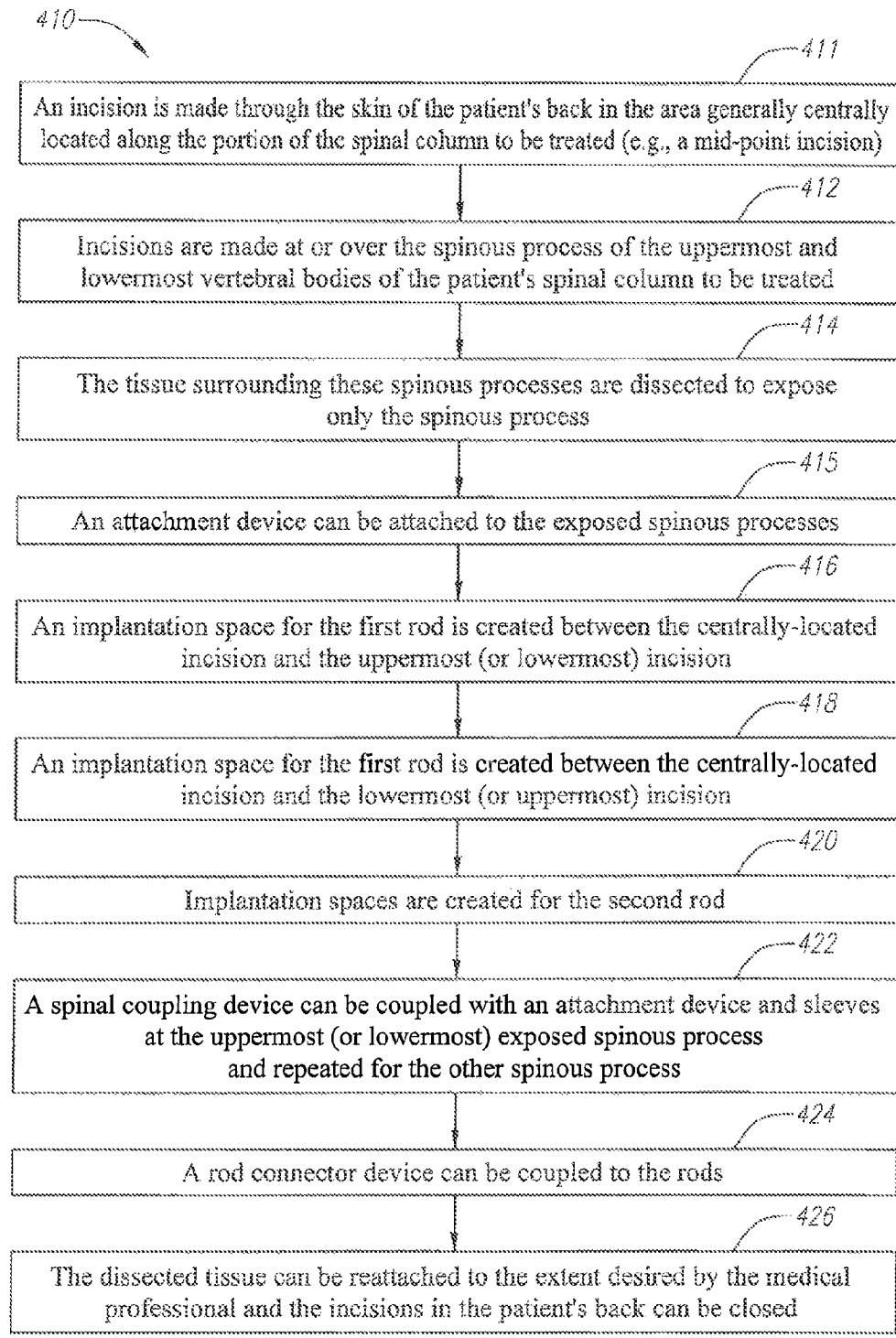

FIG. 14 is a flow diagram depicting another exemplary method 410 of implantation of a spinal correction system. Here, the method of implantation will be described with respect to implantation of spinal correction system 100 described with respect to FIGS. 2A-B. At 411, an incision is made through the skin of the patient's back in the area generally centrally-located along the portion of the spinal column to be treated (e.g., a mid-point incision). At 412, incisions are made at or over the spinous process of (preferably) the uppermost and lowermost vertebral bodies of the patient's spinal column to be treated. At 414, the tissue surrounding these spinous processes are dissected to expose only the spinous process. At 415, any desired attachment device (such as attachment devices 201 described herein) can be attached to these exposed spinous processes.

Figure 15A:
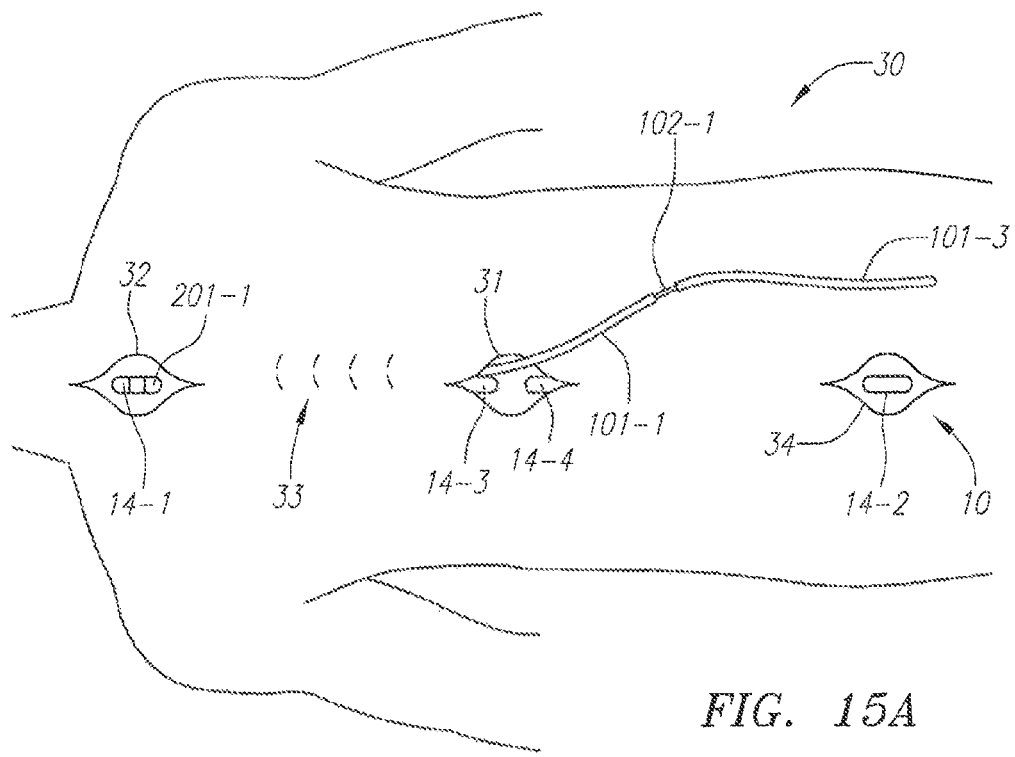
FIGS. 15A-D are perspective views depicting exemplary stages of implantation of a spinal correction system.

At 416, an implantation space is preferably created between the centrally-located incision and the uppermost incision. An example of this is depicted in the perspective view of FIG. 15A, where rod 102-1, contained within sleeves 101-1 and 101-3, is advanced from centrally-located incision 31, towards uppermost incision 32 of the patient 30 to create a first implantation space 33-1 beneath the patient's skin. Implantation space 33 is depicted as a raised portion of the patient's skin, although in practice a raised appearance may not be present. Preferably, implantation space 33 is created between each spinous process and the adjacent interspinous tissue (e.g., the interspinous ligament). Accordingly, spinous processes 14-3 and 14-4 are exposed through incision 31 to allow access to implantation spaces 33.

The use of rod 102 or a similarly shaped instrument is beneficial in that rod 102 is preferably shaped similarly to the deformity of the patient's spinal column 10 and therefore is suited to create implantation space 33 in the appropriate orientation and shape. It should be noted that any shaped or unshaped instrument can be used to create the implantation channel as desired for the application.

Implantation space 33 is preferably created in a blunt manner by advancing the distal end of rod 102-1 while within sleeve 101-1 along the spinal column 10 between each spinous process 14 and the adjacent interspinous ligament and other interspinous tissue. The distal end of rod 102-1 and sheath 101-1 is preferably relatively blunt in order to minimize the risk of inadvertently damaging spinal column 10 or the tissue and ligaments adjacent thereto. This advancement is continued until spinous process 14-1 of uppermost incision 32 is reached. One of skill in the art will readily recognize that uppermost incision 32 (or the lowermost incision) can be created before or after the rod is actually advanced along spinal column 10.

Figure 15B:
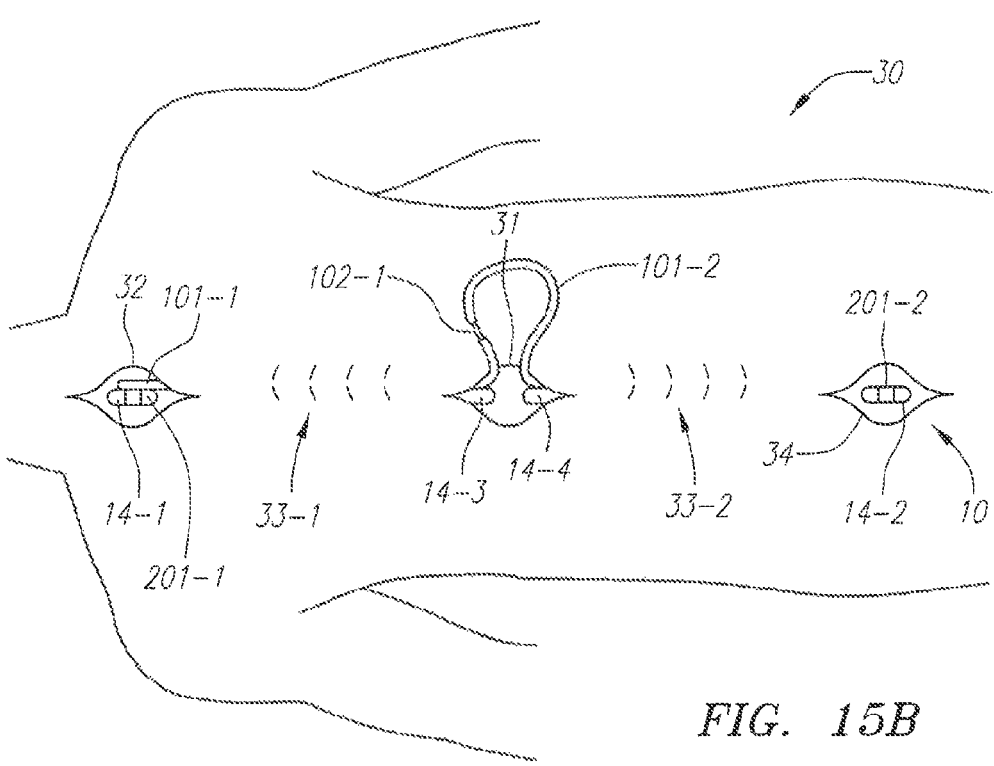

At 418, implantation space 33-2 is created between incision 31 and lowermost incision 34, again, preferably by advancing rod 102-1 and sheath 101-3 in a blunt manner. This can occur in at least several ways. First, as depicted in FIG. 15B, rod 102-1 is bent in the mid-section and the opposite end is inserted from central incision 31 towards incision 34. This is preferably possible due to the high flexibility of rod 102-1. Alternatively, rod 102-1 can be composed of a biocompatible shape memory material such as nitinol, where it can first be cooled or chilled to allow it to be easily deformed from its pre-curved shape to the bent configuration depicted here. Once inserted into the body, rod 102-1 will warm to the body's temperature and reenter the pre-curved configuration.

Figure 15C:
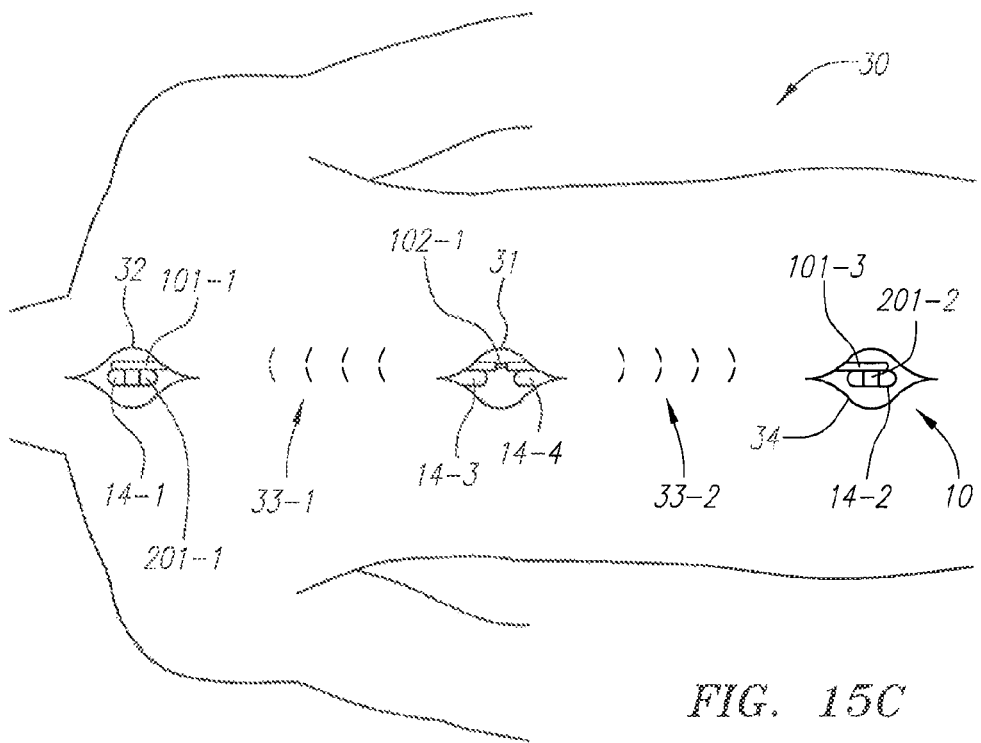

In another example, rod 102-1 is advanced from central incision 31 through implantation space 33-1 and through incision 32, until the opposing end of rod 102-1 is capable of being inserted into central incision 31. At this point, rod 102-1 can then be advanced from uppermost incision 32 past central incision 31 and along spinal column 10 until position appropriately within lowermost incision 34, as depicted in FIG. 15C.

In yet another example, as described earlier, two (or more) rod segments can be used instead of a single continuous rod. In this embodiment, a first rod segment can be inserted from the central incision 31 towards the uppermost incision 32 and a second rod segment can be inserted from the central incision 31 towards the lowermost incision 34. The rod segments can be inserted while within sleeves 101 or sleeves 101 can be inserted first. These rod segments can then be joined together by a connector, such as rigid rod connector 106 at central incision 31, which also preferably couples the rod segments to the rod (or rod segments) on the opposing side of the spinal column.

Figure 15D:
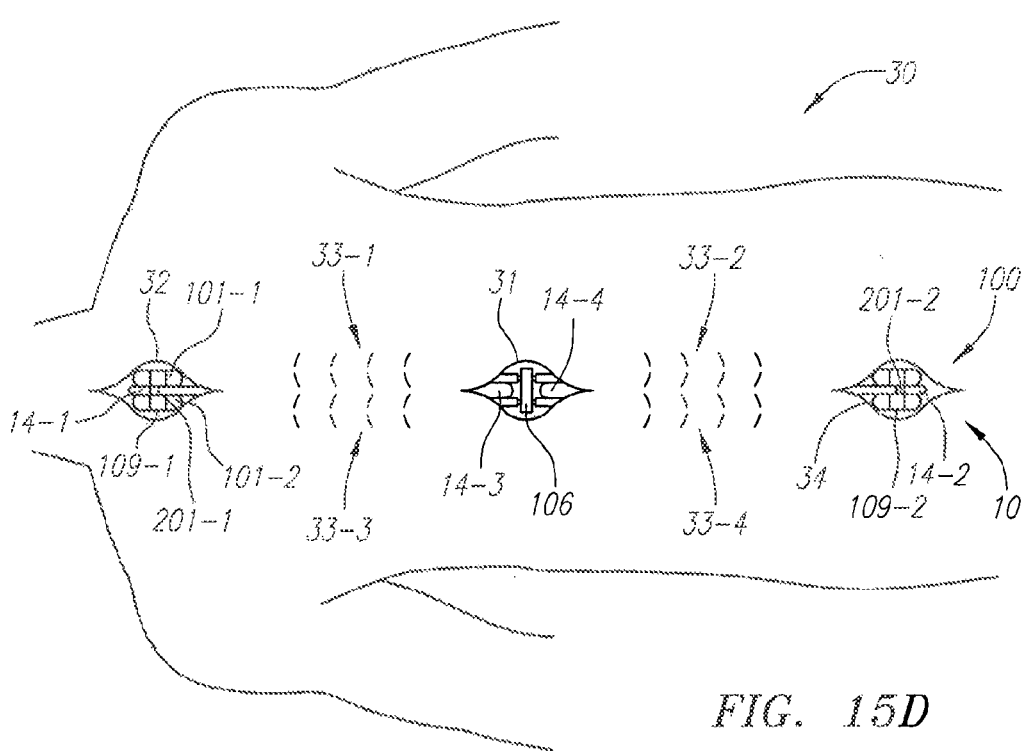

At 420, implantation spaces 33-3 and 33-4 are created for the second rod 102-2. At 422, uppermost spinal coupling device 109-1 can be coupled with attachment device 201-1 and sleeves 101-1 and 101-2. The process can be repeated and lowermost spinal coupling device 109-2 can be coupled with attachment device 201-2 and sleeves 101-3 and 101-4. At 424, rod connector device 106 is preferably coupled to rods 102-1 and 102-2. This can occur through the interspinous ligament between adjacent spinous processes 14. In this embodiment, coupling bands 108 are not used. This generally final configuration of system 100 is depicted in FIG. 15D. At 426, the dissected tissue can then be reattached to the extent desired by the medical professional and the incisions 31, 32 and 34 in the patient's back can be closed.

It should be noted that numerous variances from the above-described method can be implemented. For instance, although the uppermost and lowermost spinous processes 14-1 and 14-2 are shown to be adjacent the ends of system 100, system 100 can extend past these spinous processes further along the spinal column. In addition, the order in which system 100 is implanted can vary. For instance, instead of inserting rods 102 and sleeves 101 together to create the implantation spaces, another instrument can be first used. That instrument can be configured to create both implantation spaces for both rods at the same time. Sleeves 101 can then be placed within the implantation space followed by rods 102. Alternatively, rod 102 can be implanted first (with or without the aid of another instrument) and used as a guide over which sleeves 101 can be inserted. In this example, the sleeves can be inserted from the uppermost or lowermost incisions (or both in the case of more than one sleeve).

In another embodiment, no direct coupling is made to the spinal column at upper and lower positions. Only one incision is required to be made, preferably a centrally-located one from which system 100 can be implanted. A rod connector 106 is then preferably applied to connect rods 102, either through the interspinous ligament itself, such that the device is essentially "free-floating," or coupled directly to a spinous process.

In yet another embodiment, to create the implantation space, a thin, flexible guide instrument is first inserted along the spinal column. Sleeve 101 and rod 102 can then be attached to an end of the guide instrument and pulled through the channel created by the instrument to route sleeve 101 and rod 102 appropriately.

In a further embodiment, only lowermost and uppermost incisions are made and the centrally-located incision is foregone. In such an embodiment, the rigid connection of rods using coupling device 106 preferably occurs at least the uppermost or lowermost incisions, if not both. This implantation method can prove desirable with the implantation of shorter systems 100.

Figure 16:
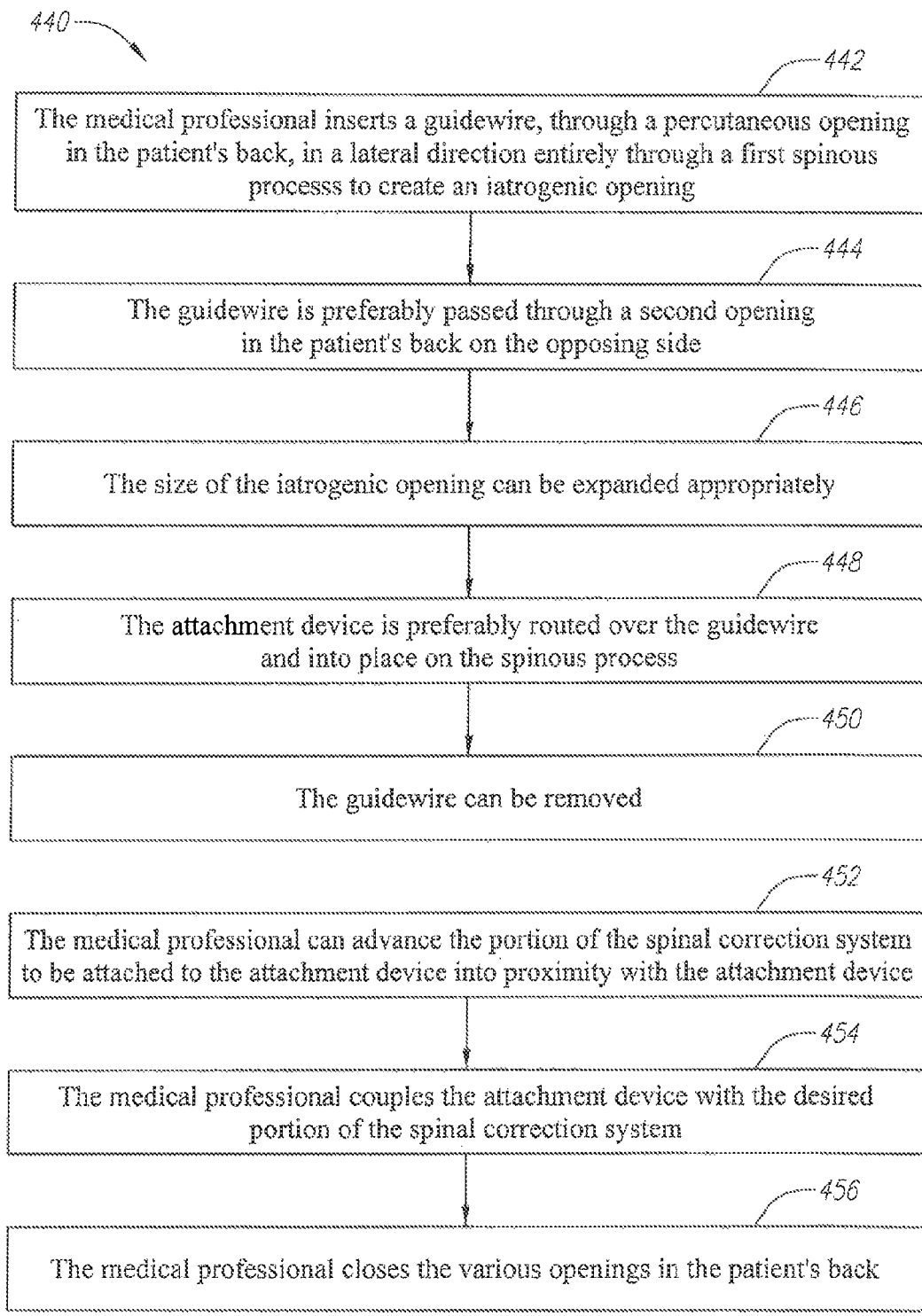
FIG. 16 is a flow chart depicting an exemplary method of implantation a spinal correction system.

FIG. 16 is a flow chart depicting another exemplary method 440 of implanting a spinal correction system 100, where the implantation of one or more attachment devices 201 occurs with the aid of a guidewire. An exemplary embodiment of an attachment device 201 configured for implantation with the aid of a guidewire is described with respect to FIG. 5G, although it should be noted that this exemplary method is not limited to such an embodiment of the attachment device.

At 442, the medical professional inserts a guidewire through a percutaneous opening in the patient's back (created by the guidewire or another instrument), in a lateral direction entirely through a first spinous process to create an iatrogenic opening. This can be accomplished with a guidewire having a sharp tip, such as a Kirschner wire (K-wire), or with another piercing instrument. Imaging, such as fluoroscopy, is also preferably employed to aid the physician in piercing the spinous process in the desired location. At 444, the guidewire is preferably passed through a second opening in the patient's back on the opposing side.

At 446, the size of the iatrogenic opening can be expanded appropriately. This can be accomplished by the iterative application of one or more dilators, each being larger than the previous dilator (or the guidewire). At 448, the attachment device is preferably routed over the guidewire and into place on (one or both sides of) the spinous process.

For instance, if using an embodiment similar to that described with respect to FIG. 5G, the attachment device 201 is placed sequentially on both sides of spinous process 14 starting with the opposing base plates 153 and 154, each advanced into position over guidewire 156 from the opening in the patient's back on each respective side of spinous process 14. It should be noted that the openings through the skin and tissue (e.g., fascia) to spinous process 14 can be sized corresponding to the largest portion of the attachment device 201 that must be advanced therethrough, thereby allowing the size of these openings to be minimized. Guide elements 152 and 155 are also advanced into place over guidewire 156 and into position over each base plate 153 and 154 after which screw 151 is advanced and used to couple the components together.

At 450, the guidewire can be removed. Then, at 452, the medical professional can advance the portion of the spinal correction system to be attached to the attachment device into proximity with the attachment device such that it can be coupled thereto. For instance, the medical professional can advance a rod (or sleeve, or rod and sleeve, etc.) through a separate opening in the patient's back and into proximity with the attachment device.

At 454, the medical professional couples the attachment device with the desired portion of the spinal correction system. For instance, in one embodiment the attachment device includes an eyelet or other housing for receiving the rod, and the rod can be routed directly through the eyelet to couple the two together, thereby requiring minimal access (and a minimal opening) for the medical professional through the laterally placed openings in the patient's back. Depending on the level of user access needed to couple the rod or component with the attachment device, the opening through which the attachment device is inserted can also be minimized. Also, the opening through which the rod or other component of the spinal correction system is inserted can be sized minimally, generally the same as that rod or component. After completion of the implantation of the spinal correction system, which may include the implantation of multiple attachment devices, then at 456, the medical professional closes the various openings in the patient's back.

Figure 17:
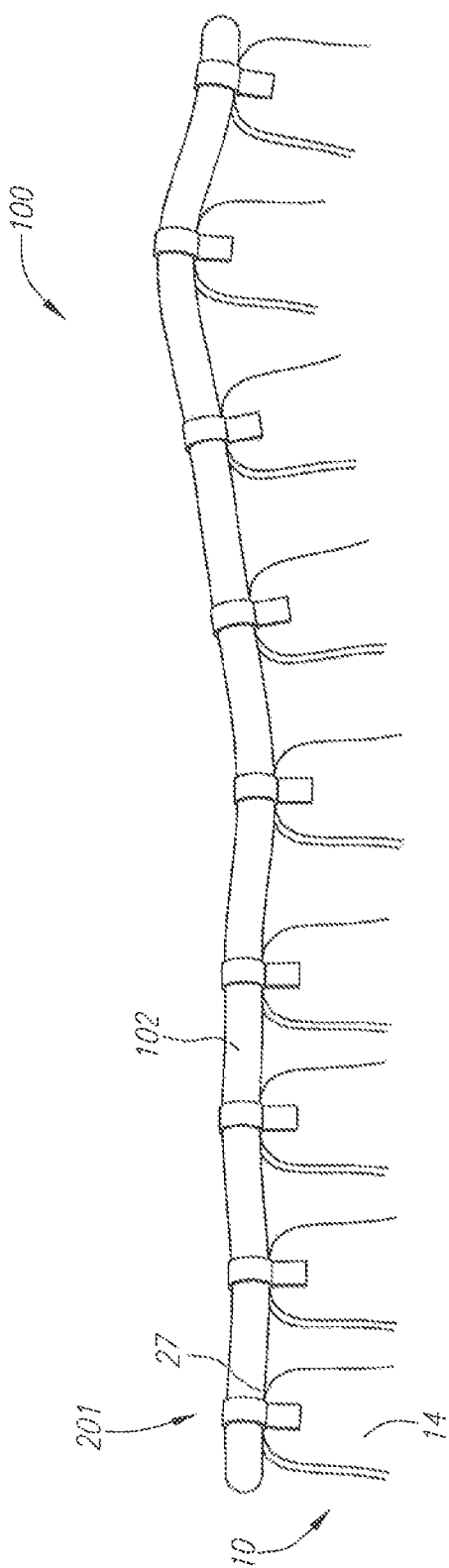
FIG. 17 is a lateral view depicting an exemplary embodiment of a spinal correction device.

Of course, if desired, a single incision can be placed along the length of the spinal column where system 100 is to be implanted, to expose the entire implantation space. This can allow for other configurations of system 100 to be implanted. FIG. 17 is a lateral view depicting another exemplary embodiment of spinal correction system 100. Here, system 100 is configured to be implanted along the posterior edges 27 of one or more spinous processes 14. Multiple attachment devices 201 are coupled on each spinous process 14 to be treated, and include a tubular portion configured to hold a rod 102. This embodiment provides the benefit of restricting exposure of spinous processes 14 to only the most posterior portion (e.g., less than 50% of the length of each spinous process 14).

Any portion of system 100 can be coated with any material as desired. Some exemplary coatings that can be used include coatings that are biodegradable, drug coatings (e.g., drugs can be released from hydrogels or polymer carriers where the polymer itself is a biodegradable material or elastomers, coatings that increase or decrease lubricity, bioactive coatings, coatings that inhibit thrombus formation, and coatings that speed the healing response.

These coatings can be applied over the entire system 100 or any portion thereof. Also, different portions of system 100 can be coated with different coatings. Furthermore, the surface topography of the elements of system 100 can be varied or configured to accelerate biodegradation of those elements (if including biodegradable materials) and/or to promote tissue encapsulation thereof.

It should be noted that various embodiments are described herein with reference to one or more numerical values. These numerical value(s) are intended as examples only and in no way should be construed as limiting the subject matter recited in any claim, absent express recitation of a numerical value in that claim.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure.

What is claimed is:

1. A method of performing a procedure for implanting a spinal correction apparatus, comprising:
    creating an access opening in the skin of a patient;
    removing tissue from a first vertebral body of the patient to expose a spinous process of the first vertebral body, wherein the tissue is removed from the first vertebral body without exposure of each facet joint of the first vertebral body; and
    coupling a first attachment device to the spinous process, wherein the attachment device is configured to allow the transmission of a corrective force from at least one elongate rod to the patient's spinal column,
    wherein the tissue of the first vertebral body is removed from the first vertebral body such that only the spinous process of the vertebral body is exposed, the method further comprising implanting the entirety of the spinal correction system, wherein the spinal correction system comprises the at least one elongate rod and a tubular member configured to slidably receive the elongate rod, and
    wherein the spinal correction system further comprises a second elongate rod, a second tubular member configured to slidably receive the second elongate rod, a rod coupling device configured to couple the rods together such that the rods are fixed in rotation with respect to each other at the point of coupling, and at least one spinal coupling device configured to couple each tubular member to the attachment device.

2. The method of claim 1, wherein the spinal correction system further comprises a coupling device configured to couple each tubular member together without coupling directly to the spinal column.

3. A method of performing a procedure for implanting a spinal correction apparatus, comprising:
    creating an access opening in the skin of a patient;
    removing tissue from a first vertebral body of the patient to expose a spinous process of the first vertebral body, wherein the tissue is removed from the first vertebral body without exposure of each facet joint of the first vertebral body; and
    coupling a first attachment device to the spinous process, wherein the attachment device is configured to allow the transmission of a corrective force from at least one elongate rod to the patient's spinal column, wherein the access opening is a first access opening located on a first side of the region of the patient's spinal column to be treated, the method further comprising:
    creating a first implantation space between a second access opening and the first access opening prior to coupling the first attachment device to the spinous process, the second access opening being located centrally in the region of the patient's spinal column to be treated; and
    creating a second implantation space between the second access opening and a third access opening, the third access opening being located on a second side of the region of the patient's spinal column to be treated.

4. The method of claim 3, further comprising implanting the at least one elongate rod within the first and second implantation spaces.

5. The method of claim 4, wherein implanting the at least one elongate rod comprises:
    advancing a first end of the rod through the second access opening towards the first access opening;
    bending the rod at a position exterior to the second access opening; and
    inserting a second end of the rod through the second access opening towards the third access opening.

6. The method of claim 4, wherein implanting the at least one elongate rod comprises:
    advancing a first end of the rod through the second access opening and through the first access opening until a second end of the rod is positioned adjacent the second access opening; and
    inserting the second end of the rod through the second access opening towards the third access opening.

7. The method of claim 4, wherein implanting the at least one elongate rod comprises inserting the rod into the implantation spaces while received within at least one tubular member.

8. The method of claim 4, wherein implanting the at least one elongate rod comprises inserting the rod into at least one tubular member positioned within at least one of the implantation spaces.

9. The method of claim 3, wherein creating the first implantation space comprises inserting a first end of the at least one elongate rod along the patient's spinal column to separate tissue to create the implantation space.

10. The method of claim 9, wherein the first end of the at least one elongate rod is inserted between a spinous process and an adjacent interspinous ligament of at least one vertebral body.

11. The method of claim 3, wherein creating the first implantation space comprises inserting a first end of an instrument along the patient's spinal column to separate tissue to create the implantation space, wherein the instrument is not implanted.

12. The method of claim 3, further comprising:
accessing a second vertebral body of the patient through the third access opening;
removing connective tissue from the second vertebral body of the patient to expose a spinous process of the second vertebral body, wherein the tissue is removed without dissection of the ligamenta flava coupled with the second vertebral body of the patient; and
coupling a second attachment device to the spinous process of the second vertebral body, wherein the attachment device is configured to allow the transmission of a corrective force from the at least one elongate rod to the patient's spinal column.

13. The method of claim 12, further comprising coupling the at least one elongate rod to the first and second attachment devices.

14. The method of claim 13, wherein the at least one elongate rod is slidably coupled within a first tubular member and a second tubular member, the first tubular member being coupled to the first attachment device and the second tubular member being coupled to the second attachment device.

15. The method of claim 13, wherein the at least one elongate rod is coupled such that the rod is located on a first lateral side of the patient's spinal column.

16. The method of claim 15, wherein the at least one elongate rod is a first elongate rod, the method further comprising implanting a second elongate rod on a second lateral side of the patient's spinal column.

* * * * *